(12) United States Patent
Hook et al.

(10) Patent No.: US 7,241,592 B2
(45) Date of Patent: Jul. 10, 2007

(54) CROSS-REACTIVE DISPLACING ANTIBODIES FROM COLLAGEN-BINDING PROTEINS AND METHOD OF IDENTIFICATION AND USE

(75) Inventors: Magnus Hook, Houston, TX (US); Yi Xu, Houston, TX (US); Pietro Speziale, Pavia (IT); Livia Visal, Rosate (IT); Fabrizia Casolini, Sondalo (IT); Joseph M. Patti, Cumming, GA (US); Pratiksha Patel, Duluth, GA (US); Paul Domanski, Atlanta, GA (US)

(73) Assignees: Universita Degli Studi di Pavia, Pavia (IT); The Texas A&M University System, College Station, TX (US); Inhibitex, Inc., Alpharetta, GA (US)

( * ) Notice: Subject to any disclaimer, the term of this patent is extended or adjusted under 35 U.S.C. 154(b) by 0 days.

(21) Appl. No.: 09/810,428

(22) Filed: Mar. 19, 2001

(65) Prior Publication Data

US 2007/0122416 A1 May 31, 2007

Related U.S. Application Data

(60) Provisional application No. 60/225,402, filed on Aug. 15, 2000, provisional application No. 60/199,370, filed on Apr. 25, 2000, provisional application No. 60/189,968, filed on Mar. 17, 2000.

(51) Int. Cl.
| | |
|---|---|
| C12P 21/08 | (2006.01) |
| C12N 1/00 | (2006.01) |
| A61K 39/395 | (2006.01) |
| A61K 39/40 | (2006.01) |
| C07K 16/12 | (2006.01) |

(52) U.S. Cl. ............... 435/69.7; 435/340; 435/332; 435/331; 435/326; 530/350; 530/387.1; 530/388.1; 530/388.4; 424/130.1; 424/131.1; 424/133.1; 424/134.1; 424/137.1; 424/138.1; 424/141.1; 424/176.1; 424/177.1; 424/237.1; 424/139.1; 424/150.1; 424/165.1

(58) Field of Classification Search ............ 424/130.1, 424/131.1, 133.1, 134.1, 137.1, 138.1, 141.1, 424/176.1, 177.1, 237.1, 139.1, 150.1, 165.1, 424/164.1; 514/2, 12; 530/350, 387.1, 388.1, 530/388.4; 435/326, 331, 340, 697
See application file for complete search history.

(56) References Cited

U.S. PATENT DOCUMENTS 6,288,214 B1 * 9/2001 Hook et al.

FOREIGN PATENT DOCUMENTS

WO    WO 97/43314    11/1997

OTHER PUBLICATIONS

Patti et al ( Journal of Biological Chemistry. May 1992, vol. 267. No. 7, pp. 4764-4772).*
Schiotz et al Acta.Pathol Microbiol Scand 1979, 87(6) 329-36.*
Espersen et al (Acta.Pathol Microbiol Scand 1981, 89:253-260).*
Longshaw et al Microbiology 2000, 146; 1419-1427.*
Patti et al Biochemistry. Oct. 26, 1993; 32(42): 11428-35.*
Symersky et al Nat. Struct Biol. Oct. 1997; 4(10): 833-8.*
Foster et al., Surface protein adhesion of *Staphylococcus aureus*, Trends in Microbiology 1998, vol. 6, No. 12, pp. 484-488.
Symersky et al., Structure of the Collagen-binding domain from a *Staphylococcus aureus* adhesion, Nature Structural Biology, Oct. 1997, vol. 4, No. 10, pp. 833-838.
Patti, Critical Residues in the Ligand-binding site of the *Staphylococcus aureus* collagen-binding adhesion (MSCRAMM), Journal of Biological Chemistry, May 1995, vol. 270, No. 20, pp. 12005-12011.
Nehal Mohamed, Mark A. Teeters, Joseph M. Patti, Magnus Hook, Julia M. Ross; Inhibition of *Staphylococcus aureus* Adherence to Collagen under Dynamic Conditions; Feb. 1999; pp. 589-594; vol. 67, No. 2; Infection and Immunity.

Lech M. Switalski, Joseph M. Patti, Wade Butcher, Anthony G. Gristina, Pietro Speziale, Magnus Hook; A collagen receptor on *Staphylococcus aureus* strains isolated from patients with septic arthritis mediates adhesion to cartilage; 1993; pp. 99-107; vol. 7, No. 1; Molecular Microbiology.

Joseph M. Patti, Jeffrey O. Boles, Magnus Hook; Identification and Biochemical Characterization of the Ligand Binding Domain of the Collagen Adhesin from *Staphylococcus aureus*; Oct. 26, 1993; pp. 11428-11435; vol. 32, No. 42; Biochemistry.

Visal et al., "Monoclonal Antibodies to CNA, a Collagen-binding Microbial Surface Component Recognizing Adhesive Matrix Molecules, . . . ", The Journal of Biological Chemistry, vol. 275, No. 51, Issue of Dec. 22, 2000, pp. 39837-39845.

Patti et al., "Identification and Biochemical Characterization of the Ligand Binding Domain of the Collagen Adhesin from *Staphylococcus aureus*", Biochemistry 1993, 32, pp. 11428-11435.

Imundo et al., "Cystic fibrosis epithelial cells have a receptor for pathogenic bacteria on their apical surface", *Proc. Natl. Acad. Sci. USA*, vol. 92, pp. 3019-3023, Mar. 1995, Medical Sciences.

* cited by examiner

*Primary Examiner*—Jeffrey Siew
*Assistant Examiner*—Padma Baskar
(74) *Attorney, Agent, or Firm*—B. Aaron Schulman; Stites & Harbison, PLLC

(57) ABSTRACT

Antibodies to the CNA protein and to other regions from the collagen binding domain, including domain CNA19, are provided, and antibodies produced in this manner have been shown to be cross reactive to both *Staphylococcus aureus* and *Staphylococcus epidermidis* bacteria and which can thus be used in the prevention and treatment of infections caused by both of these types of bacteria. In addition, medical instruments can be treated using the antibodies of the invention in order to reduce or eliminate the possibility of their becoming infected or further spreading the infection. In particular, the proteins are advantageous because they are cross-reactive and may thus be administered to patients so as to reduce or prevent severe infection by staphylococcal bacteria of more than one species. Antibodies generated in this manner have also been shown to exhibit displacement activity and can thus be utilized advantageously in methods wherein these antibodies will be administered to patients having pre-existing staphylococcal infections because of the ability to displace bacterial proteins from binding sites on the extracellular matrix. Finally, a method of identifying, isolating and utilizing displacing antibodies is also provided.

8 Claims, 27 Drawing Sheets

Figure 1:
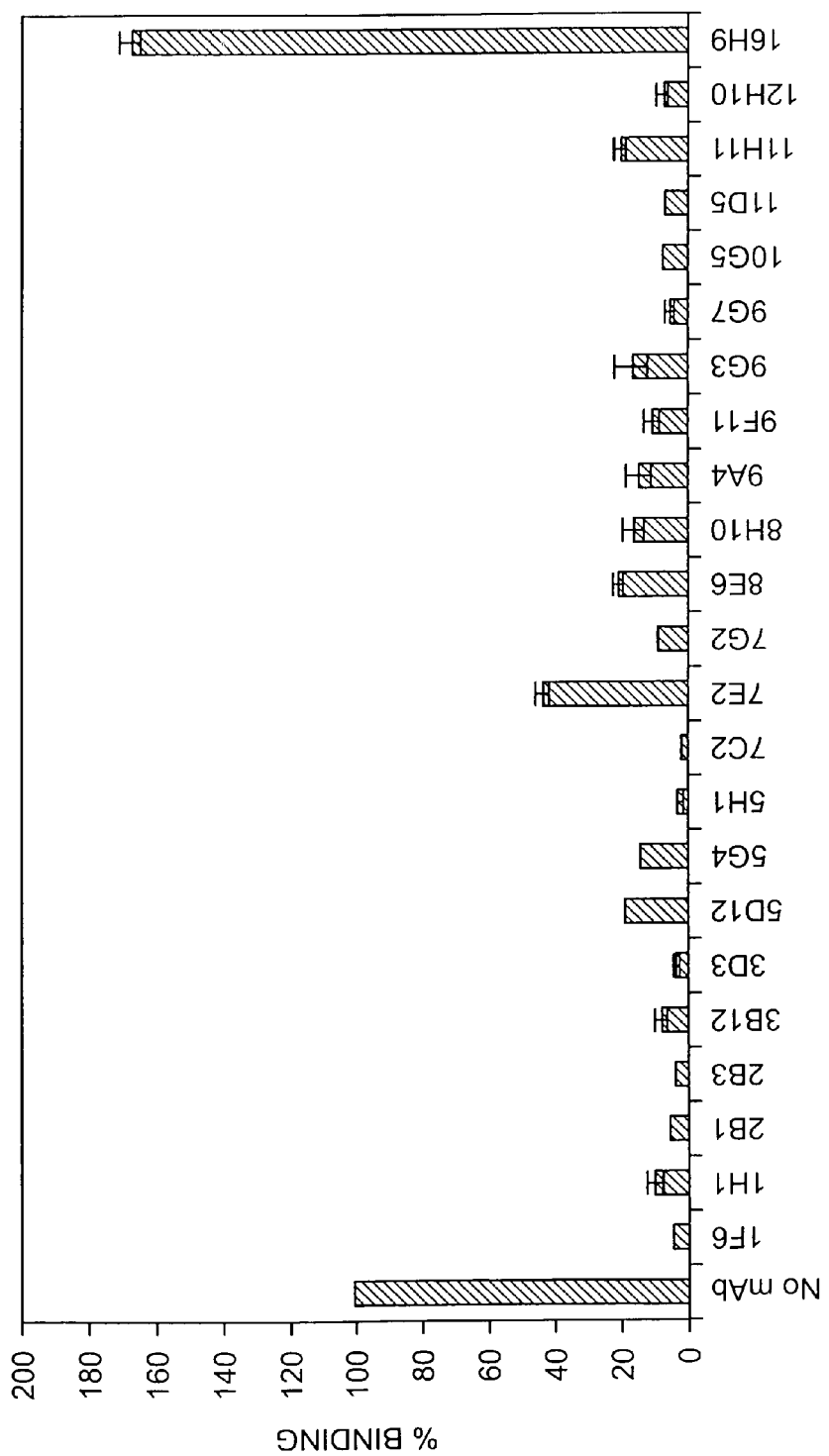

```
                                    βA*                          βB*
CNA19 : -ITSGNKSTNVTVHKSEAGTSS---VEVXKTGDMLPEDTTHVRWFENI
ACE19 : TATATQRLTIEGVTNTETGQIERDYPFFXKVGDLAGE--SNQVRWFLNV
             βC                βD*              βA*      α1

βH*
CNA19 : NNEKSYVSKDLLKDQIQGGQQLDLSTLNINMTGTHSNYYSGQSAITD
ACE19 : NLNKSDVTEDSIADRQGSGQENKESFTFDIVNDKETKMIS---LAE
             βF               βG                 βJ

α2
CNA19 : FEKAFPGSKTVDNTKNTIDVTIPQGYGSYNSESINYKTKITNE--QQ
ACE19 : FEQQGYG--KIDFV-EDNDFNERFYRDKARETSFIVRYTSTITEAGQHQ
             βI

CNA19 : KEFVNNSQAWYQEHGKEEVNGKSFNHTVHN
ACE19 : ATFENSYDINYQLNNQDATNEKNTSQVKNV
```

FIG. 2A

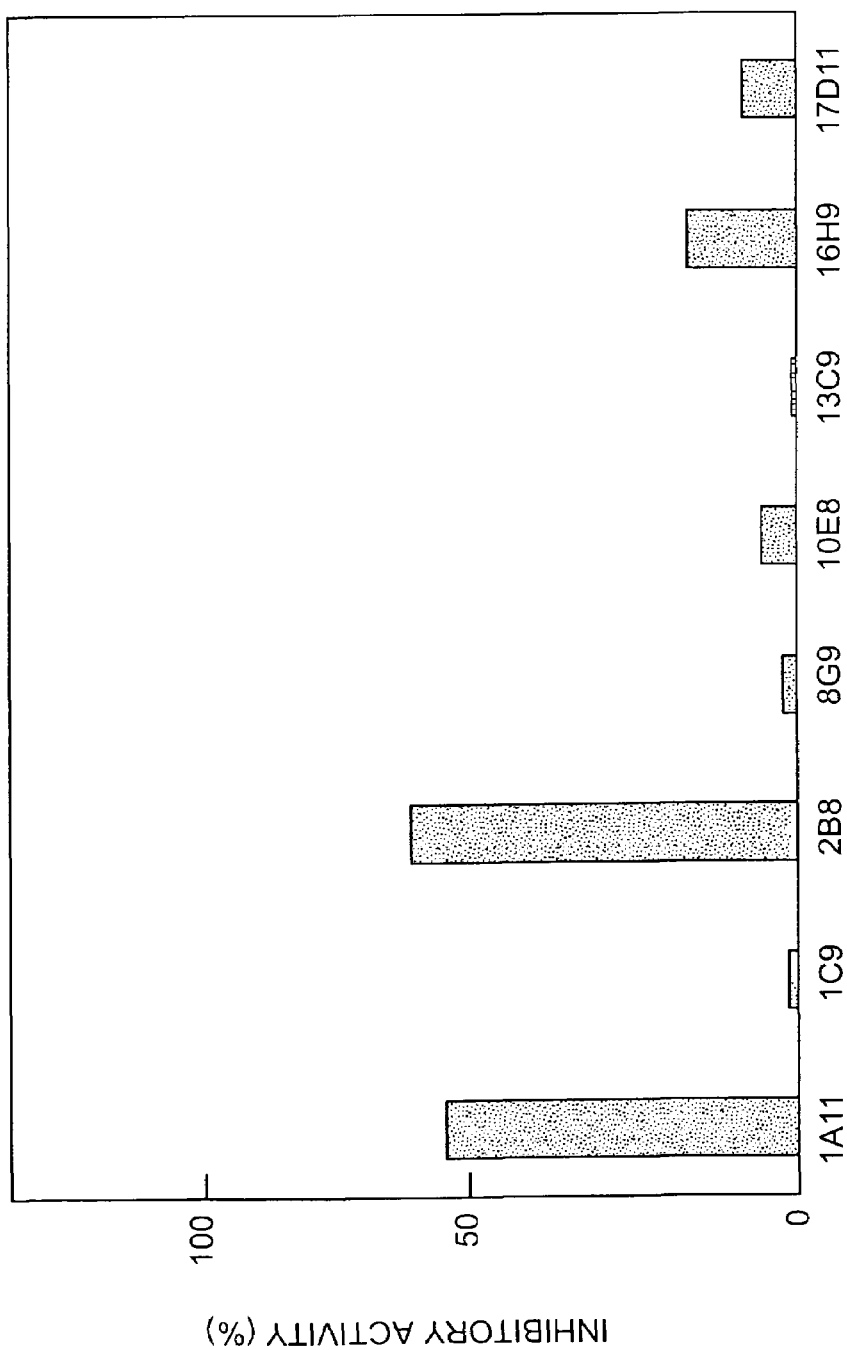

CROSS-REACTIVE DISPLACING ANTIBODIES FROM COLLAGEN-BINDING PROTEINS AND METHOD OF IDENTIFICATION AND USE

CROSS-REFERENCE TO RELATED APPLICATIONS

This application claims the benefit of U.S. Provisional Patent Application No. 60/225,402, filed Aug. 15, 2000, U.S. Provisional Patent Application No. 60/199,370, filed Apr. 25, 2000, and U.S. Provisional Patent Application No. 60/189,968, filed Mar. 17, 2000.

FIELD OF THE INVENTION

The present invention relates in general to displacing antibodies which can inhibit collagen binding to *Staphylococcus aureus* bacteria and to methods for developing and utilizing displacing antibodies, and in particular to antibodies to CNA, the collagen adhesin of *Staphylococcus aureus*, and its subregions, which are cross-reactive to multiple strains of *S. aureus* and to *S. epidermidis*, and which can be used to inhibit collagen binding to *S. aureus* and in a variety of compositions and methods for the therapeutic or preventive treatment of infections from *S. aureus* and *S. epidermidis*.

BACKGROUND OF THE INVENTION

*Staphylococcus aureus* is a bacterial pathogen that is capable of colonizing a wide range of host tissues and causing infections such as endocarditis, wound infections, pneumonia, osteomyelitis and septic arthritis. The initial attachment and colonization on host tissues is thought to be the first crucial step in the disease development. Staphylococci produce a family of surface proteins named MSCRAMMs (Microbial Surface Component Recognizing Adhesive Matrix Molecules) that mediate adherence to extracellular matrix (ECM) proteins. Collagen is a major ECM protein and is the main component of tissues such as skin, bone, tendon, cartilage and teeth. It is conceivable that the *S. aureus* developed strategies to utilize collagen as a way to colonize host tissues.

Several studies have supported this notion. For example, *S. aureus* cells retrieved from infected joints were shown to be predominantly attached to the cartilage (1). Switalski et al. demonstrated that a collagen-binding MSCRAMM, CNA, was necessary and sufficient for *S. aureus* to attach to cartilage in vitro (2). Furthermore, CNA was shown to be a virulence factor in experimental septic arthritis (3). CNA+ strains showed dramatically increased virulence compared with the isogenic CNA− strains as evaluated by the clinical symptoms and histopathological patterns of the joints. No viable *S. aureus* cells were recovered from the joints of mice injected with the CNA− strains, while significant numbers of *S. aureus* cells were isolated from the joints of those injected with the CNA+ strains. In addition, vaccination with a recombinant fragment of CNA protected mice from septic death against intravenous challenge with *S. aureus* (4).

Other bacteria that have been reported to express collagen-adhesins include certain strains of *Escherichia coli* (5), *Yersinia enterocolitica* (6–8), *Klebsiella pneumoniae* (9), *Streptococcus mutans* (10,11), group A streptococci (12), *Streptococcus gordonii* (11,13), *Enterococcus faecalis* (14), *Lactobacilli reuteri* (15) and *Lactobacilli crispatus* (T. K. Korhonen, personal communication). The collagen-adhesin YadA was shown to contribute to the arthritogenicity of *Y. enterocolitica* in a rat model (16). Substitution of two histidine residues in YadA with alanine abrogated collagen binding and cell adherence, and caused reduced virulence in mice (17), suggesting that these functions of YadA were related. Mammalian proteins that interact with collagen include extracellular matrix proteins (e.g., fibronectin, decorin, thrombospondin and von Willebrand factor) and cell receptors (e.g., integrins $\alpha_1\beta_1$ and $\alpha_2\beta_1$). Their interactions mediate processes such as cell adhesion and migration, platelet aggregation, and tumor metastasis. Therefore, a deeper understanding of the interactions between collagen and the staphylococcal adhesin will not only contribute to our understanding of the molecular pathogenesis of staphylococcal infections but also provide insight of how collagen-binding proteins in general interact with this ligand.

Previous studies showed that CNA recognized triple helical collagen as well as some synthetic peptides that formed a collagen-like triple helix (18). CNA was found to contain typical elements of surface proteins of gram-positive bacteria. It consists of a signal peptide, a non-repetitive A domain, several repeats (B domains), followed by a cell-wall anchor region, a transmembrane segment and a short cytoplasmic tail. The A domain of CNA (CNA55) was found to be fully responsible for the collagen-binding activity of CNA (19). The minimum binding domain was localized to a 19 kDa fragment, CNA19 (formerly designated CBD (151–318)), within CNA55 (19). The crystal structure of CNA19 was solved (20). The structure was composed of two antiparallel β-sheets and two short α-helices. β-strands A, B, part of D, E and H form β-sheet I, and strands C, part of D, F, G, I and J form β-sheet II. A trench was observed in β-sheet I into which a triple helical collagen molecule fits as shown by docking experiments using theoretical collagen probes of $[(Gly-Pro-Pro)_4]_3$ or $[(Gly-Pro-Hyp)_4]_3$. Site-directed mutagenesis of some residues in the trench of CNA19 abolished collagen binding (Y175K, R189A, F191A, N193K, and Y233A) or caused reduced binding affinity (N223K and N278K) (20,21), indicating that the trench was essential for binding. Two truncates of CNA19 that had the N-terminal 30 amino acids or the C-terminal 22 amino acids removed respectively were generated. The C-terminal truncate, CBD (151–297), did not bind collagen, while the N-terminus truncate was insoluble. The N-terminal truncate contains all but 6 of the residues in the trench and the C-terminal truncate contains all the residues, suggesting that the intact CNA19 molecule is important in presenting the trench in an active collagen-binding conformation. Structural analysis on the I domains of integrins $\alpha_1\beta_1$ and $\alpha_2\beta_1$, the collagen binding domains, also indicated the presence of trench-like structures (22–24). Mutations of some residues along the wall of the trench in the I domain of $\alpha_2\beta_1$ affected collagen binding (25–28). Thus, it seems that using a trench structure as the site of interaction for collagen may be a general theme.

Recently, a collagen-adhesin (ACE) of *Enterococcus faecalis* was identified (14). ACE has similar domain organization as CNA, a signal peptide sequence, a collagen-binding region (A) followed by repeated segments (B repeats), and elements required for surface display. The A domain of ACE shares sequence similarity with the A domain of CNA in the corresponding segments and these parts of the two proteins appear to be structurally related as determined by far-UV circular dichroism analysis of the ACE A domain (14). This raised the possibility that there may also be a trench structure in the ACE A domain and the trench may be the binding site for collagen.

However, with regard to Staphylococcal bacteria, it has still remained a problem to identify and utilize the information concerning the collagen binding site so as to develop methods of more efficiently preventing and/or treating staph infections. In addition, it has still been a goal of the study of the collagen binding activity of to develop methods and compositions which could be useful in treating or preventing infections from more than one type of staph infection. Finally, it is even further desirable in the field of infectious diseases to development compositions which are particularly successful not only in preventing staph infection, but in treating existing infection by displacing proteins already bound at sites on the extracellular matrix in cells of a human or animal patient.

SUMMARY OF THE INVENTION

Accordingly, it is an object of the present invention to provide antibodies to the CNA19 minimal collagen binding region of S. aureus which is also cross-reactive so as to recognize the collagen binding region of both S. aureus and S. epidermidis.

It is a further object of the present invention to provide an antibody to a collagen binding region which can be useful in inhibiting collagen binding by staphylococcal bacteria of more than one species.

It is a further object of the present invention to provide antibodies and antisera which will prevent the adherence of staphylococcal bacteria to the extracellular matrix proteins such as collagen and which will also be capable of displacing MSCRAMMs that are already bound to sites on the extracellular matrix.

It is a further object of the present invention to provide passive vaccines which can be used in treating or preventing infection by Staphylococcal bacteria, including *Staphylococcus aureus* and *epidermidis*.

It is still further an object of the present invention to generate antisera and antibodies to the CNA protein and its collagen binding domains including CNA19 which can also be useful in developing methods of treatment which can inhibit binding of collagen to staphylococcal bacteria and thus be employed in order to treat or prevent staphylococcal infection.

It is a further object of the present invention to provide improved materials and methods for detecting and differentiating collagen-binding proteins in staphylococcal organisms in clinical and laboratory settings.

It is a further object of the invention to provide nucleic acid sequences which code for the variable light sequence and the variable heavy sequences from the monoclonal antibodies of the present invention.

It is even further an object of the present invention to develop more effective and efficient ways of utilizing antibodies against collagen binding proteins in staphylococci so as to produce suitable compositions which can inhibit or displace the attachment of staphylococcal bacteria to collagen and which can thus be useful in improved therapeutic methods of treating of preventing staphylococcal infection.

These and other objects are provided by virtue of the present invention which comprises the isolation and use of monoclonal antibodies to the CNA protein and its subregions, including the CNA19 peptide, and monoclonal antibodies generated in this fashion have been shown to be cross-reactive with more than one *Staphylococcus* species of bacteria. In accordance with the present invention, monoclonal antibodies (mAbs) that were capable of inhibiting the binding of staphylococcal bacteria to host cells are provided, and in addition, antibodies to CNA19 which can recognize S. aureus as well as S. epidermidis are provided in accordance with the invention.

In another aspect of the present invention, since it was shown that recognition was conformation-dependent, the present invention includes chimeric proteins between CNA19 and a segment of the ACE A domain that were generated and used successfully to map epitopes within CNA19 which were functionally relevant.

Still further, characterizations of antibodies raised to the CNA19 peptide in accordance with the invention have indicated that CNA19 mAbs have inhibitory effects on an S. aureus strain binding to soluble collagen as well as attachment to immobilized collagen. Moreover, some of these antibodies have exhibited displacing behavior and thus these antibodies could effectively release S. aureus from preformed collagen-bacteria complexes as well as detach S. aureus from the surface of immobilized collagen. A model of the interactions between collagen and the different conformational states of CNA19 and contemplated clinical applications of these displacing mAbs as therapeutic agents is also provided in accordance with the invention.

In addition, as indicated herein, murine monoclonal antibodies generated against CNA19 from S. aureus in accordance with the present invention have been shown to be cross-reactive in that they recognized 5 different clinical isolates of S. epidermidis and thus may be useful in developing antibody compositions that are effective in preventing or treating infections from more than one species of Staphylococcal bacteria.

Even further, the present invention relates to the discovery of a class of displacing antibodies which can be isolated and utilized in methods of treating or preventing bacterial infection. In addition, the invention provides a method for identifying and isolating displacing antibodies and for antibodies identified and isolated by the present method.

Accordingly, in accordance with the invention, antibodies raised against the CNA19 region of the collagen binding domain are provided and can be utilized in cross-reactive methods of treating or preventing bacterial infections from more than one species of bacteria, such as S. aureus and S. epidermidis, along with compositions containing said antibodies, diagnostic test kits which contain the appropriate antibodies or antisera raised against CNA19 or other regions of the collagen binding protein which can enable one to identify these bacteria in infections.

These embodiments and other alternatives and modifications within the spirit and scope of the disclosed invention will become readily apparent to those skilled in the art from reading the present specification and/or the references cited herein.

BRIEF DESCRIPTION OF THE DRAWING FIGURES

FIG. 1. Inhibition of the binding of $^{125}$I-collagen to immobilized CNA19. CNA19 recombinant protein was immobilized onto microtiter wells (1 µg in 100 µl) and probed with $^{125}$I-collagen ($8\times10^4$ cpm) in the presence of 2 µg of each mAb. Binding of $^{125}$I-collagen to CNA19 in the absence of antibody was set as 100% binding. Bars represent means±standard deviations with duplicate testing.

FIG. 2A. Sequence alignment of CNA19 and ACE19. ClustalW with default parameters was used. Shaded amino acid residues were identical and similar residues. The β-strands and α-helices of CNA19 determined by X-ray crystallography were indicated by dark bars above the corresponding regions of CNA19. β-strands A, B, a part of D, E and H are the ones that form the observed trench and are indicated by *. Sequences for CNA19 are identified as SEQ ID NOS. 5 to 8, and sequences for ACE19 are identified as SEQ ID NOS. 8 to 12.

Figure 2B:
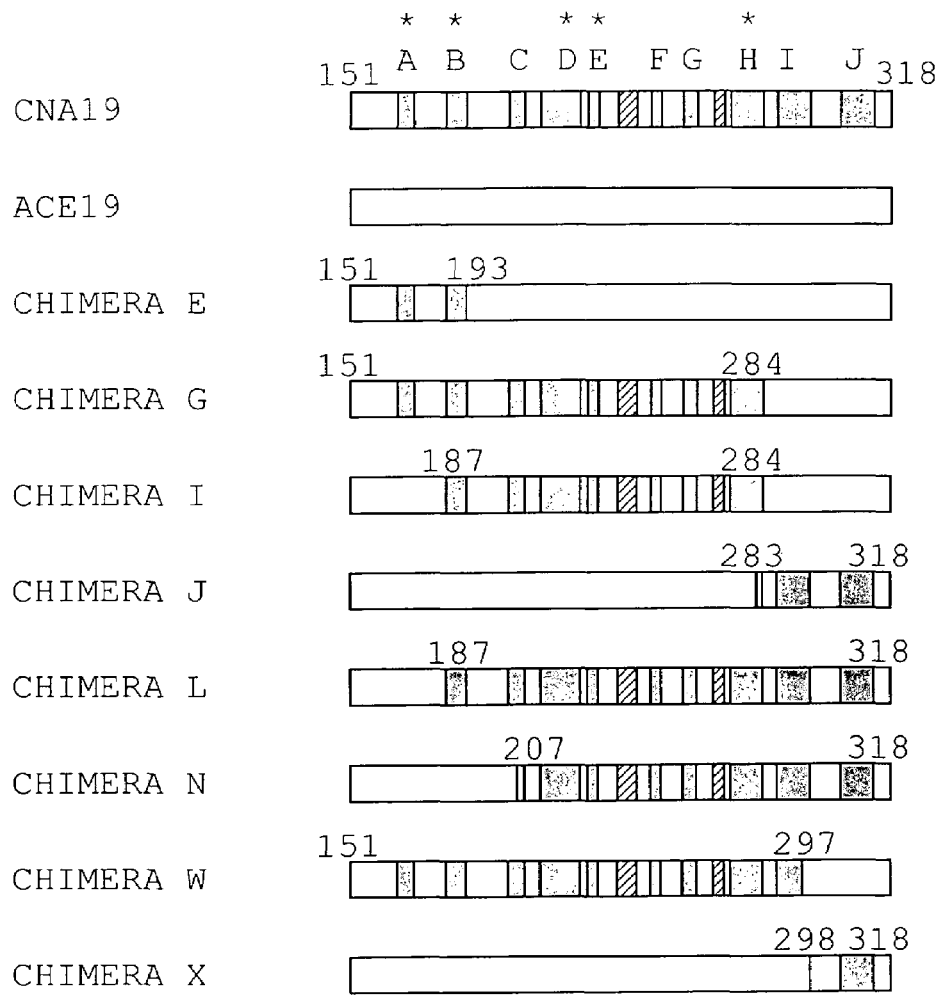

FIG. 2B. Schematic illustration of the chimeras. CNA19 sequences were represented by shaded bars while ACE19 by blank bars. Dark-shaded boxes represent β-strands and striped boxes α-helices of CNA19. "*" indicates the β-strands that form the trench. The numbers indicate the positions of the amino acid residues in CNA19.

Figure 3:
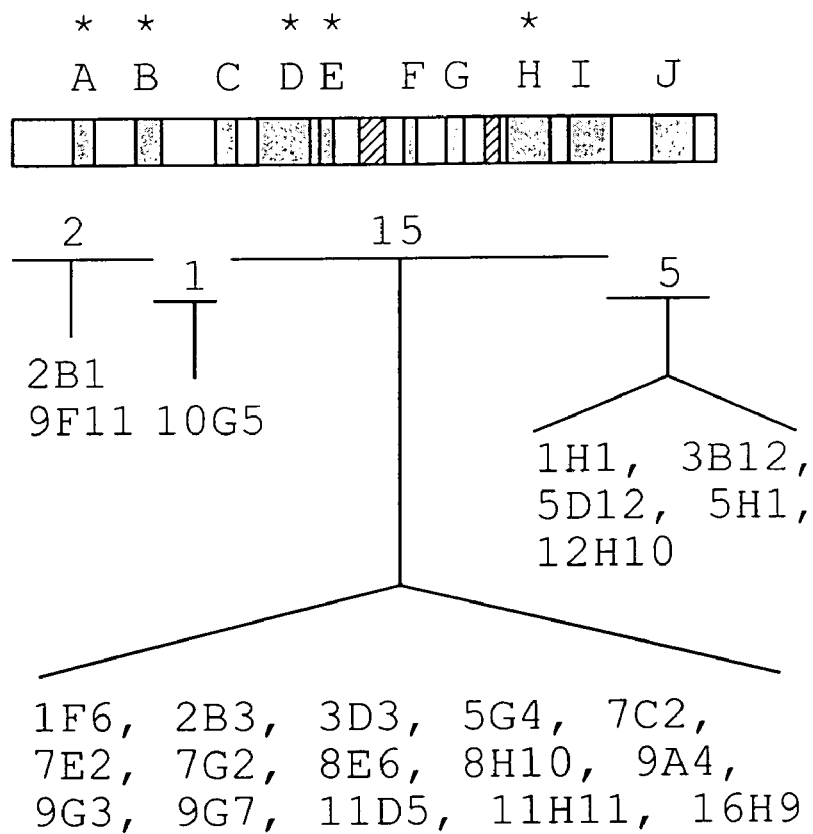

FIG. 3. Summary of the localization of CNA19 epitopes recognized by the mAbs. Horizontal lines beneath CNA19 represent regions where various mAbs were mapped, numbers above each line indicate number of mAbs in the region. The number for the central region includes 16H9, but does not include anti-His tag mAb 7E8.

Figure 4:
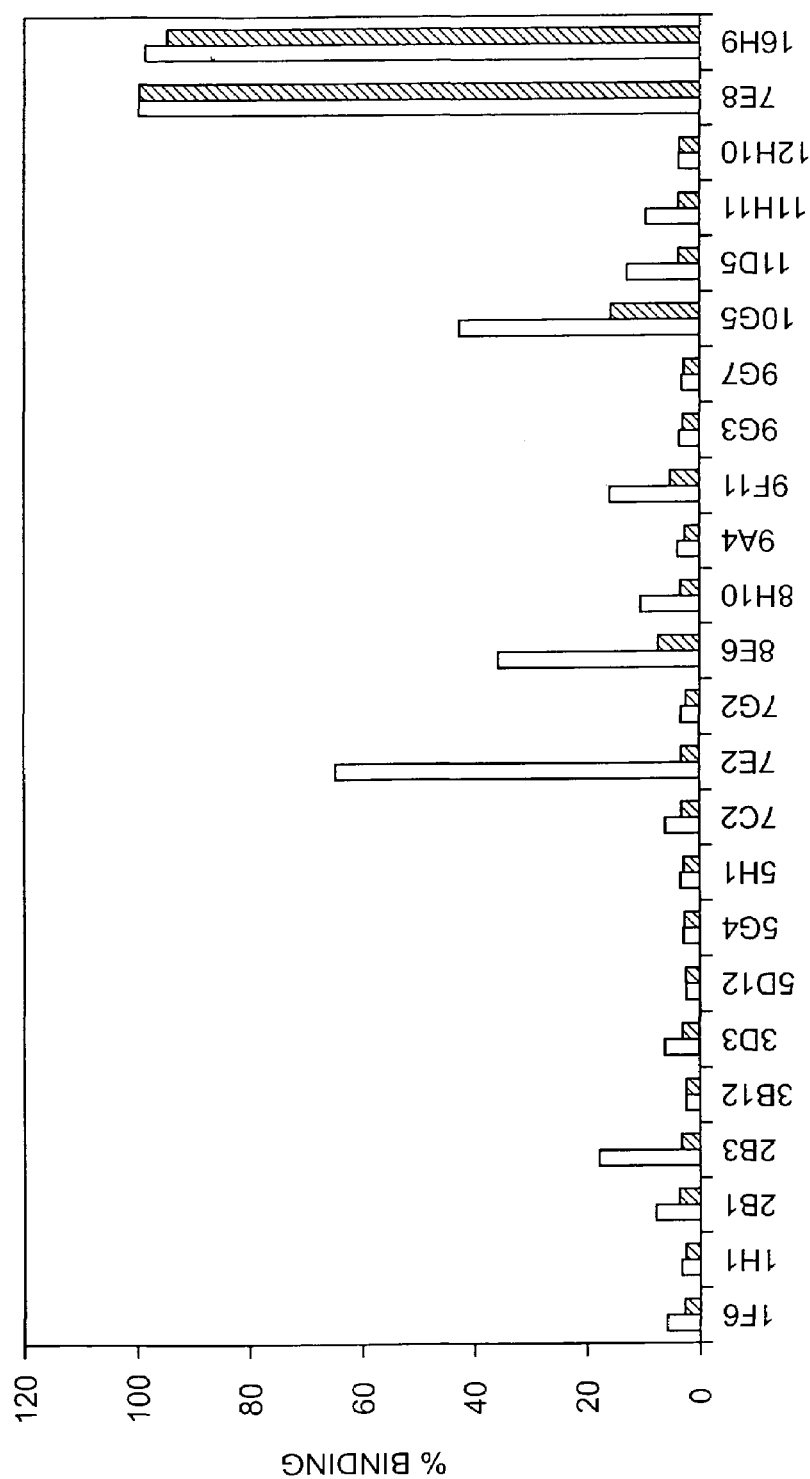

FIG. 4. Effect of anti-CNA19 mAbs on $^{125}$I-collagen binding to S. aureus Cowan 1. S. aureus Cowan 1 ($5\times10^8$ cells) were pre-incubated with the indicated amounts of each mAb prior to the addition of $^{125}$I-collagen ($5\times10^4$ cpm). Collagen binding was quantitated as described under "Experimental Procedures". Values are expressed as percentage of the ligand binding in the absence of mAb. Results are expressed as mean±standard deviation of duplicate measurements.

Figure 5:
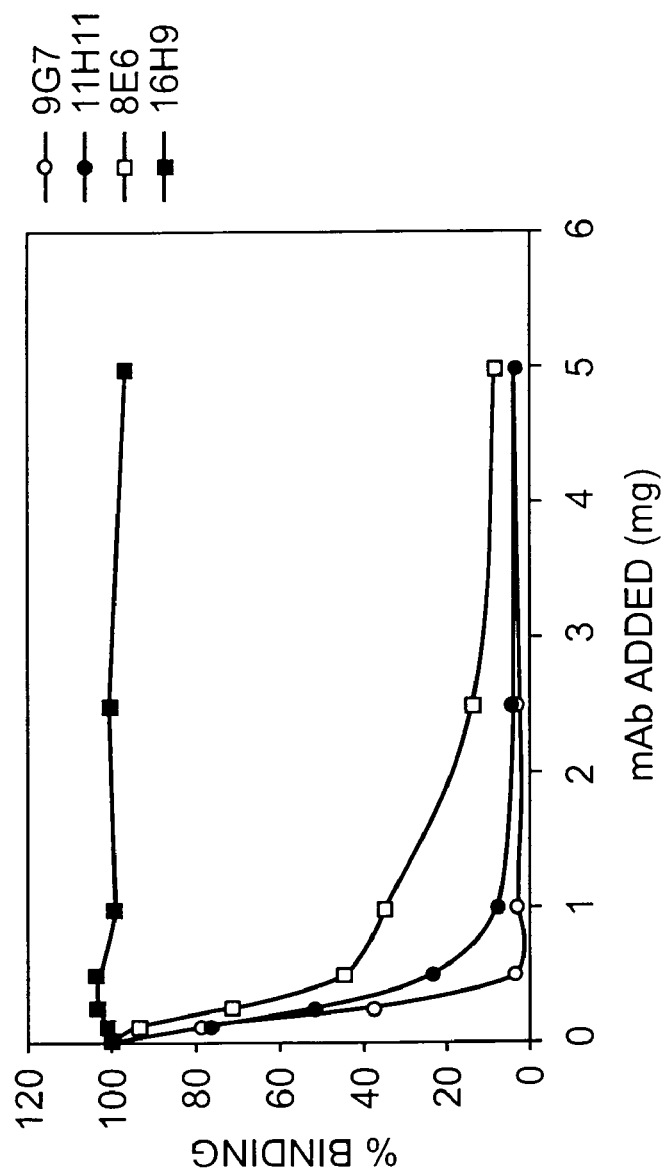

FIG. 5. Dos-dependent inhibition of $^{125}$I-collagen binding to S. aureus cells by mAbs. S. aureus Cowan I cells ($5\times10^8$ cells) were pre-incubated with increasing concentrations of mAbs 9G7, 11H11, 8E6 and 16H9 before the addition of $^{125}$I-collagen. Values are expressed as the percentage of ligand binding to bacteria in the absence of antibody and represent the mean±standard deviation of duplicate measurements.

Figure 6:
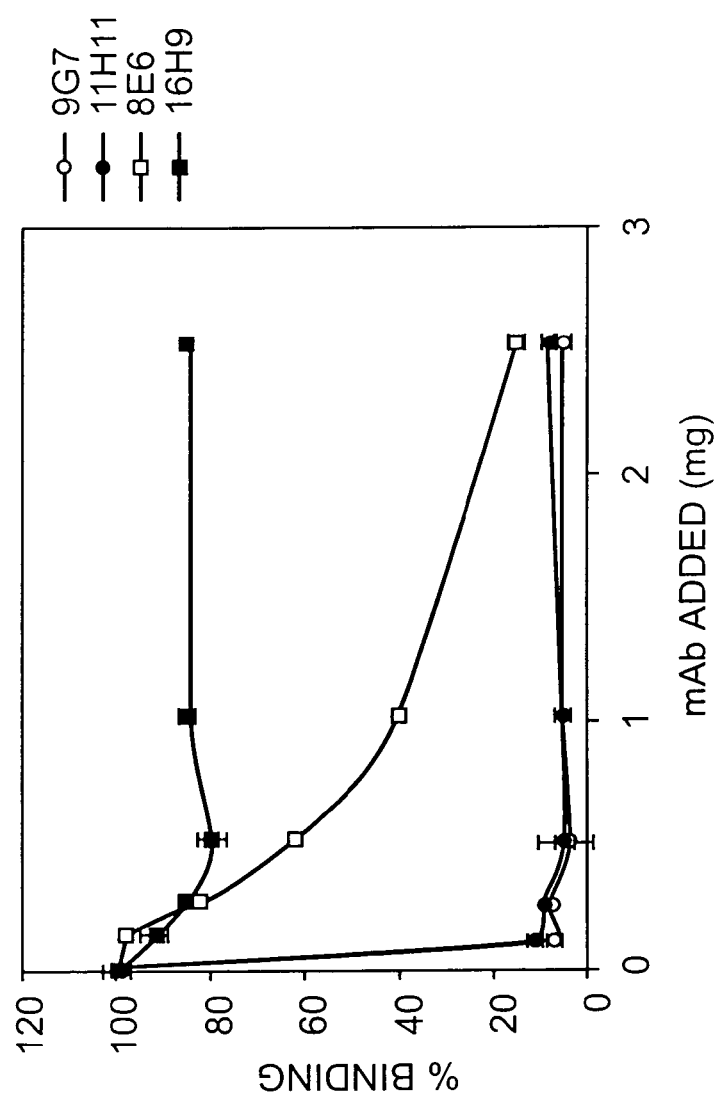

FIG. 6. Dose-dependent inhibition of S. aureus adherence to immobilized collagen by mAbs. Microtiter wells were coated with collagen type II as reported in the Examples section below. Bacterial cells were pre-incubated with increasing amounts of the indicated mAbs before being added to the wells. Adherence values are expressed as percentage of the adherence obtained in the absence of antibody. Bars represent means±standard deviations. Each sample was done in duplicate.

Figure 7:
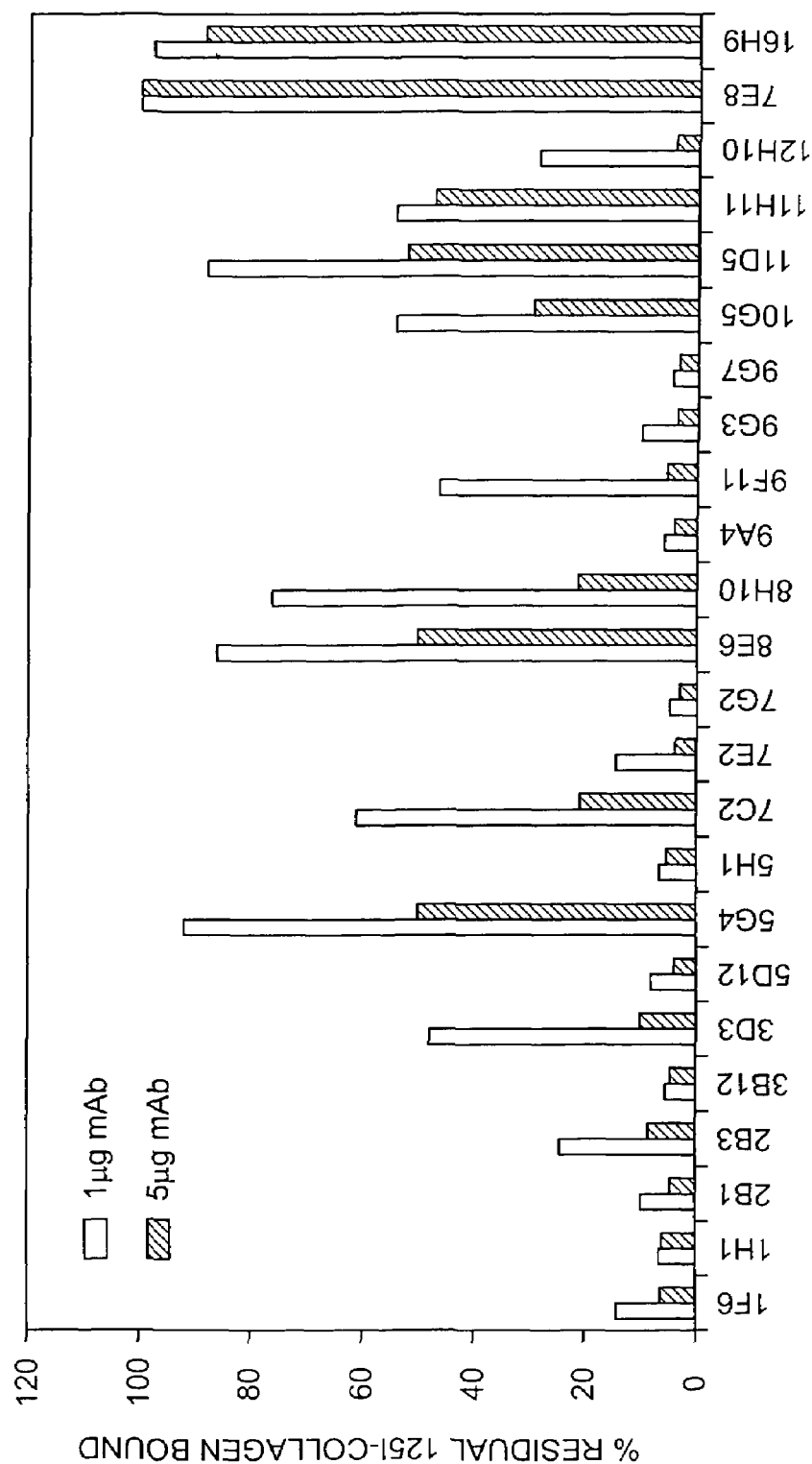

FIG. 7. Displacement of $^{125}$I-collagen from collagen-bacteria complex. S. aureus Cowan I cells ($5\times10^8$) were pre-incubated with $^{125}$I-collagen ($5\times10^4$ cpm) for 1 h. After centrifugation, bacteria-collagen complex was resuspended, and the indicated amounts of each mAb were added to the suspension and further incubated for 1 h. The amount of the residual collagen bound to bacteria was determined in a γ counter. Duplicate samples were used for each data point.

Figure 8A:
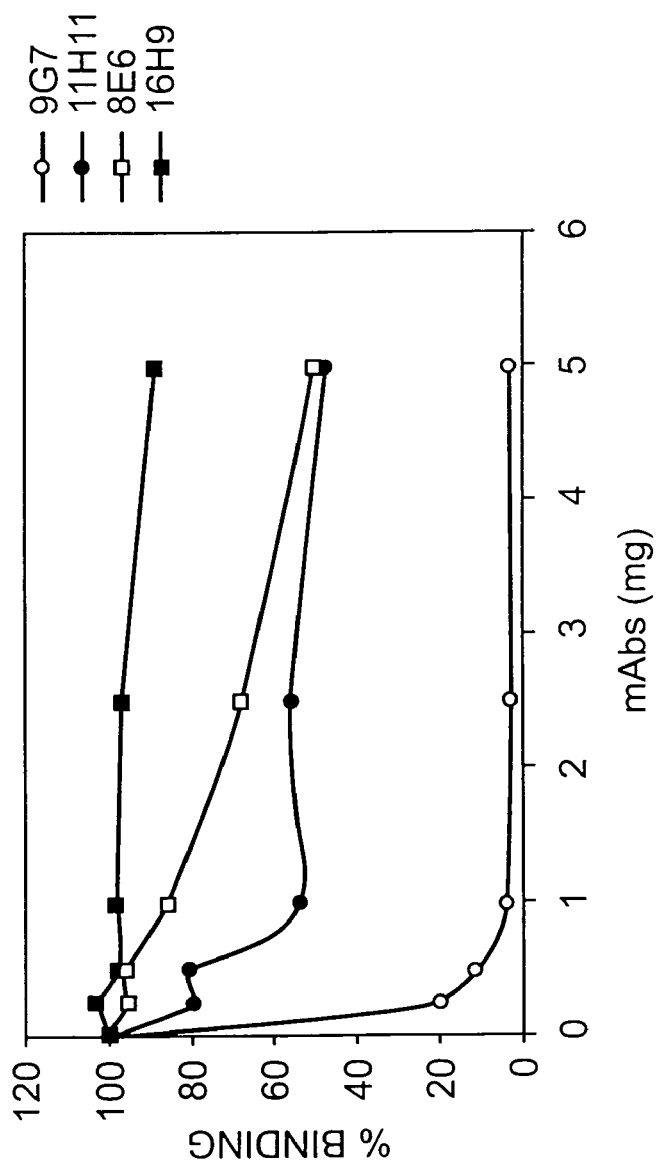

FIG. 8A. Dos-dependent displacement of $^{125}$I-collagen from collagen-staphylococci complex by mAbs. S. aureus cells were pre-incubated with $^{125}$I-collagen as reported in FIG. 7. Increasing amounts of indicated mAb were added to the bacteria-collagen complexes and incubated for 1 h. Residual $^{125}$I-collagen associated with bacteria was quantitated in a γ counter. Bars represent standard deviations from the means of duplicate measurements.

Figure 8B:
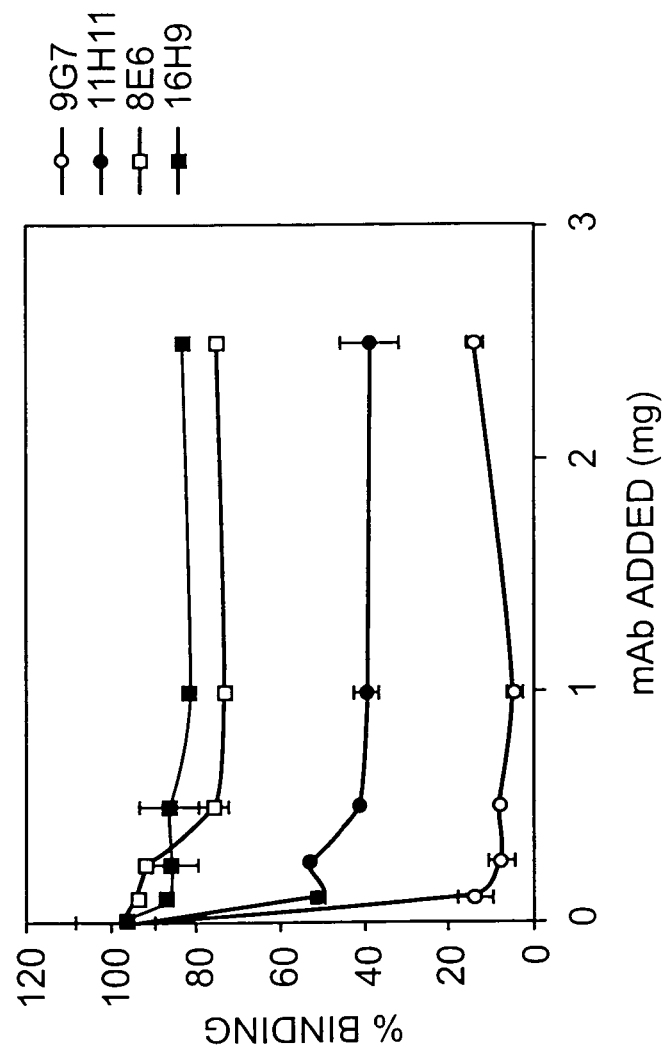

FIG. 8B. Displacement of S. aureus cells adherent to immobilized collagen by mAbs. S. aureus Cowan 1 cells were allowed to adhere to collagen coated plates. After washing, the indicated amounts of mAbs were added to the wells and incubated for 2 h. After extensive washing, the number of residual attached bacteria was quantitated by using peroxidase-conjugated rabbit anti-mouse IgG as reported in "Experimental Procedures". Data are expressed as percentage of attached bacteria in the absence of mAbs. The values are averages of incubations performed in duplicate.

Figure 9:
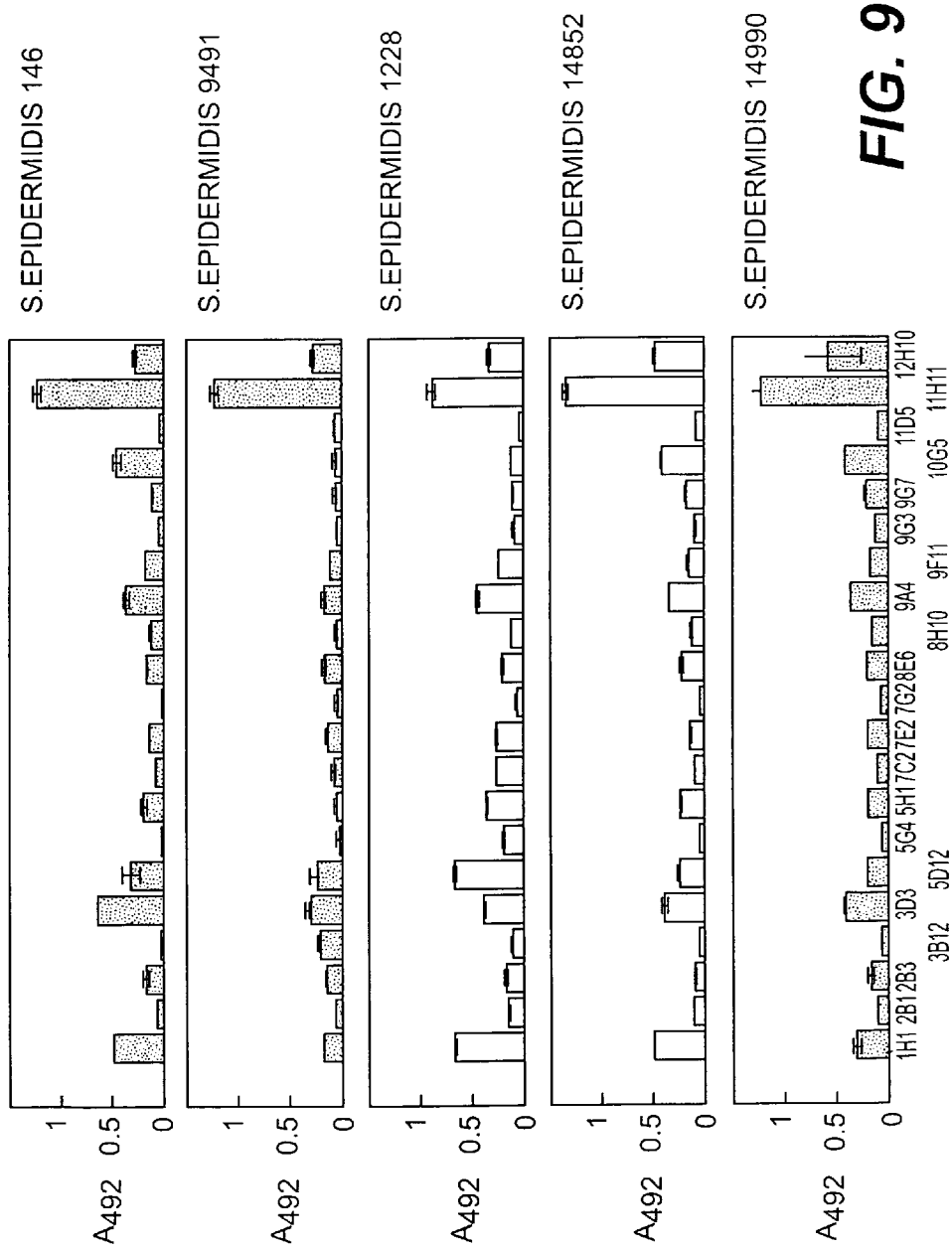

FIG. 9. Cross-reactivity of monoclonal antibodies generated against S. aureus CNA19. Cross-reactivity of monoclonal antibodies raised against S. aureus CNA19 was established via ELISA screening showing recognition of intact S. epidermidis. The graphs in this figure reflect this recognition by measuring binding of monoclonal antibodies generated against CNA19 to the five S. epidermidis strains. As shown in this figure, Mab 11H11 recognized 5 different clinical isolates of S. epidermidis. Several other Mabs, including 3D3, 9A4, and 12H10, had lower but detectable binding.

Figure 10:
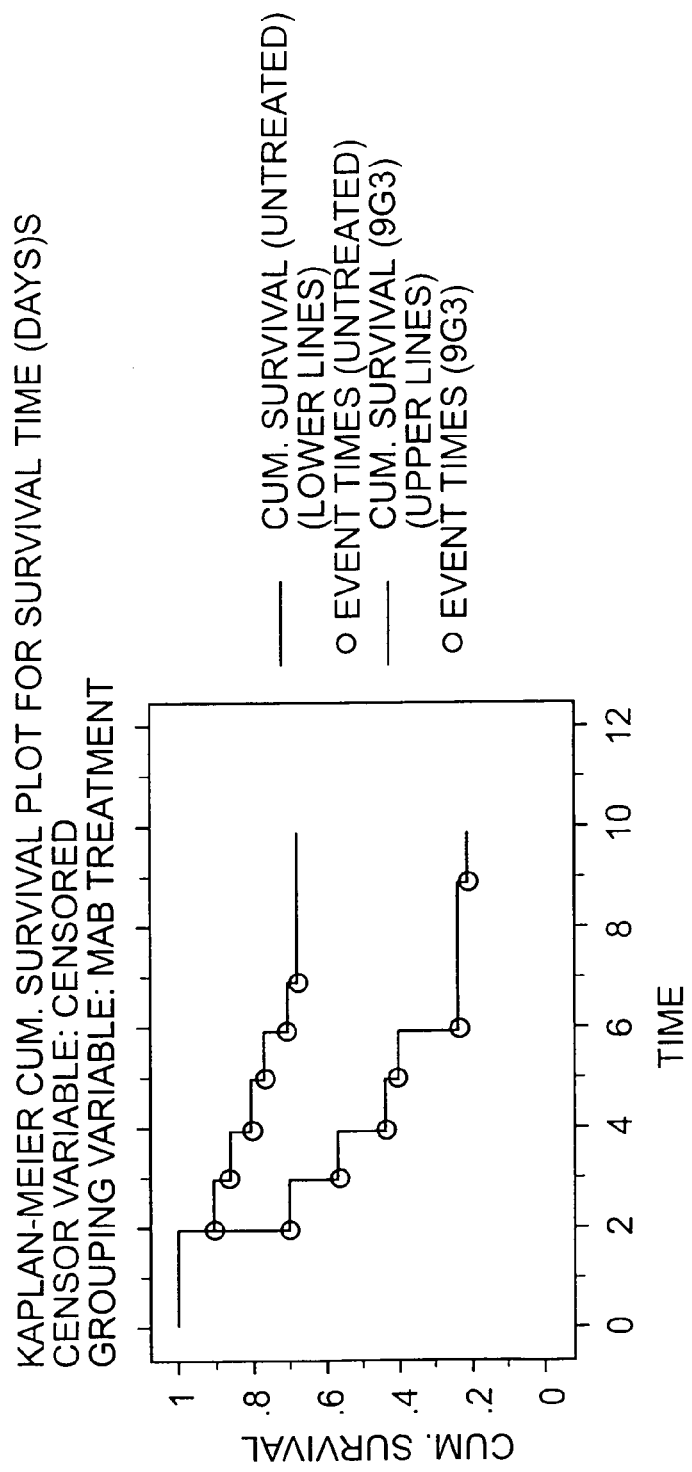

FIG. 10. Survival plot for animals treated with the 9G3 monoclonal antibody in accordance with the present invention versus untreated animals.

Figure 11:
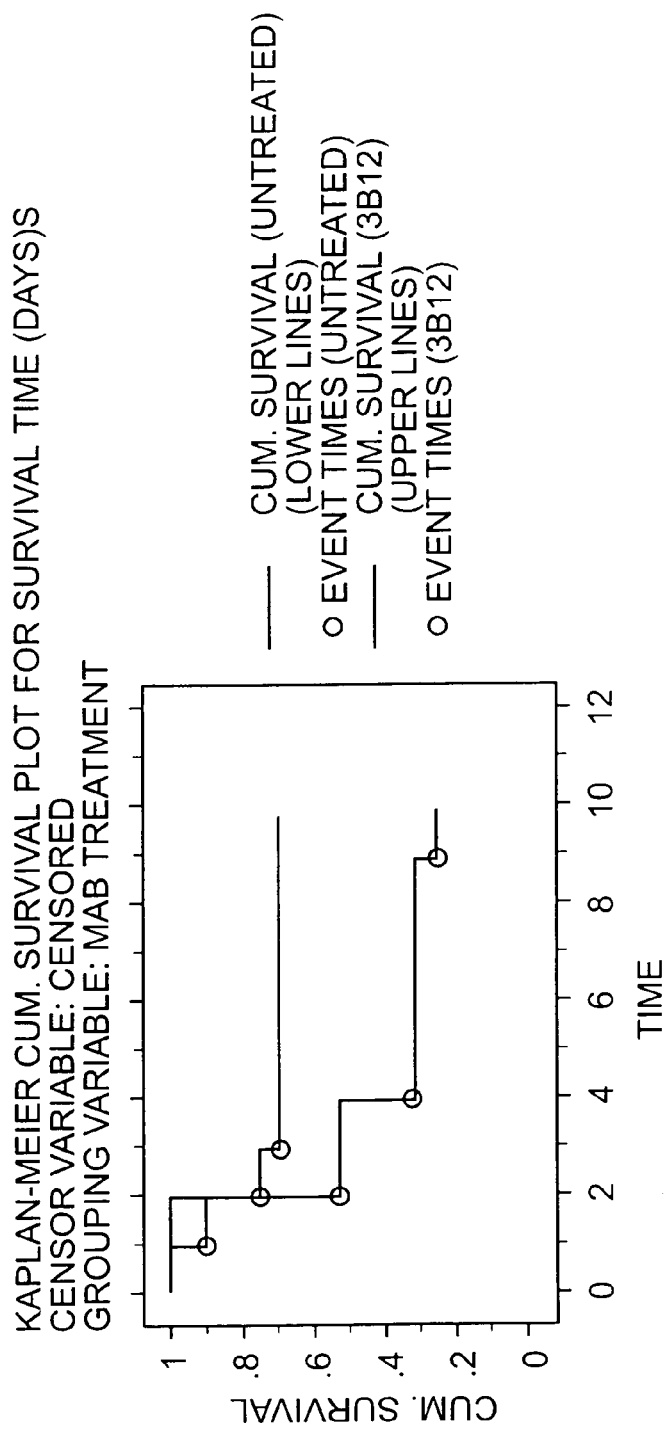

FIG. 11. Survival plot for animals treated with the 3B12 monoclonal antibody in accordance with the present invention versus untreated animals.

Figure 12A:
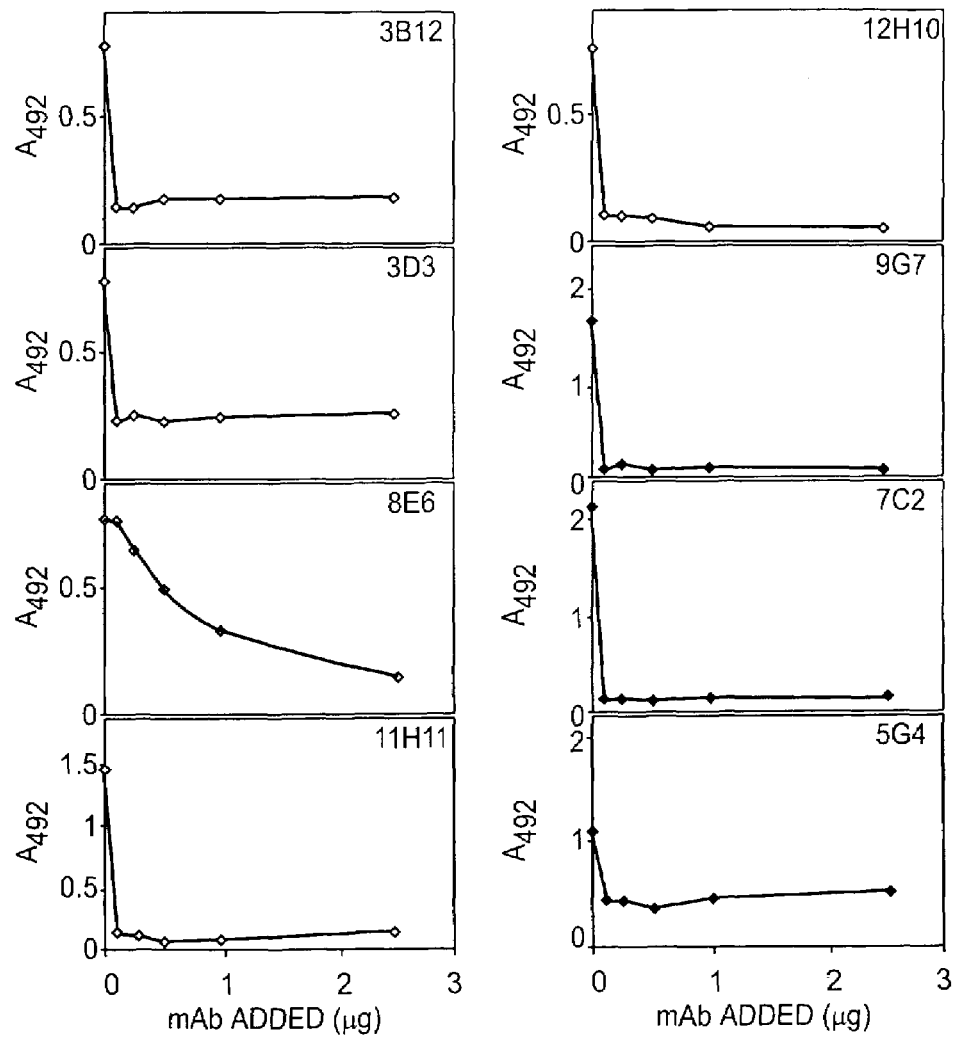
Figure 12B:
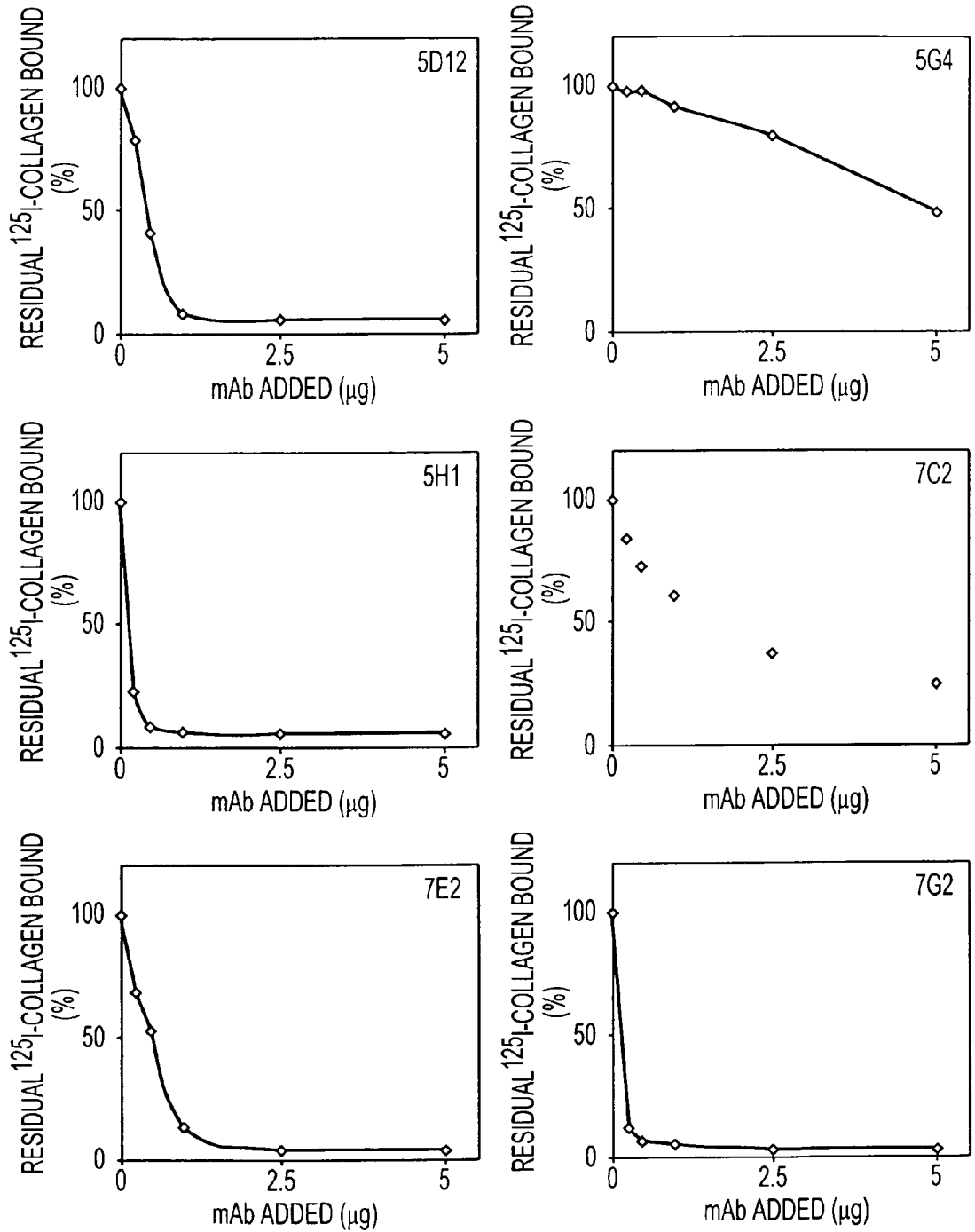

FIGS. 12A and 12B. Inhibition of S. aureus cells adherence to immobilized collagen by mAbs generated against CNA19 (CBD 151–318).

Figure 13:
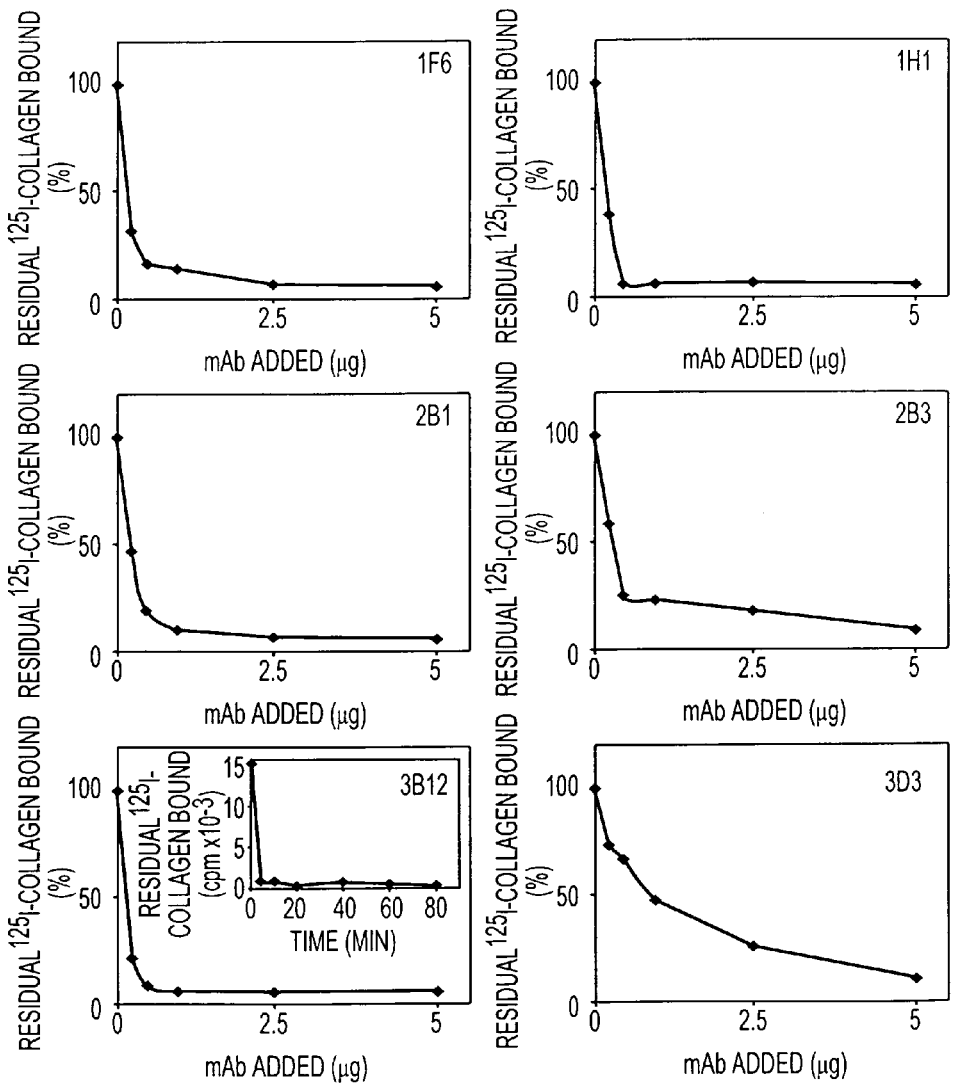

FIG. 13. Displacement of $^{125}$I-collagen from S. aureus cells by mAbs generated against CNA19 (CBD 151–318).

Figure 14A:
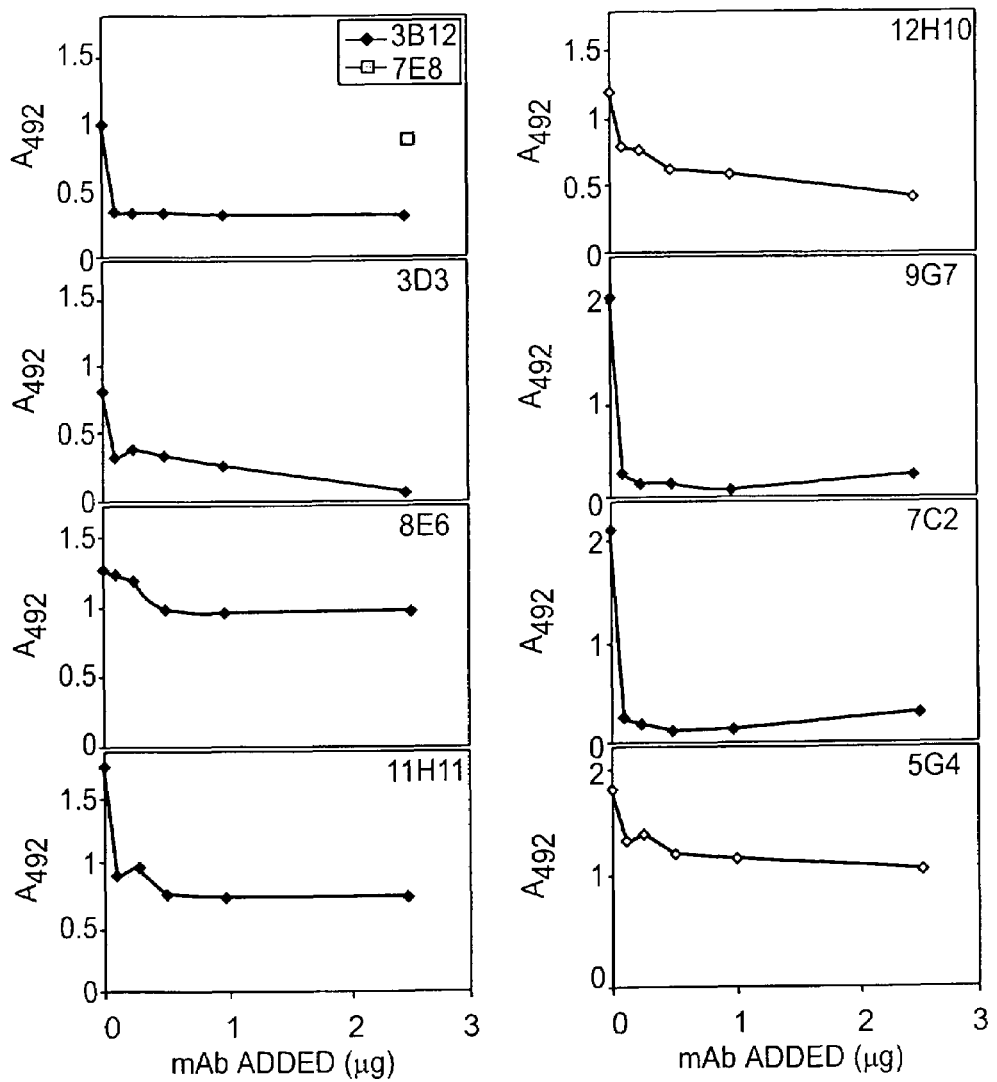
Figure 14B:
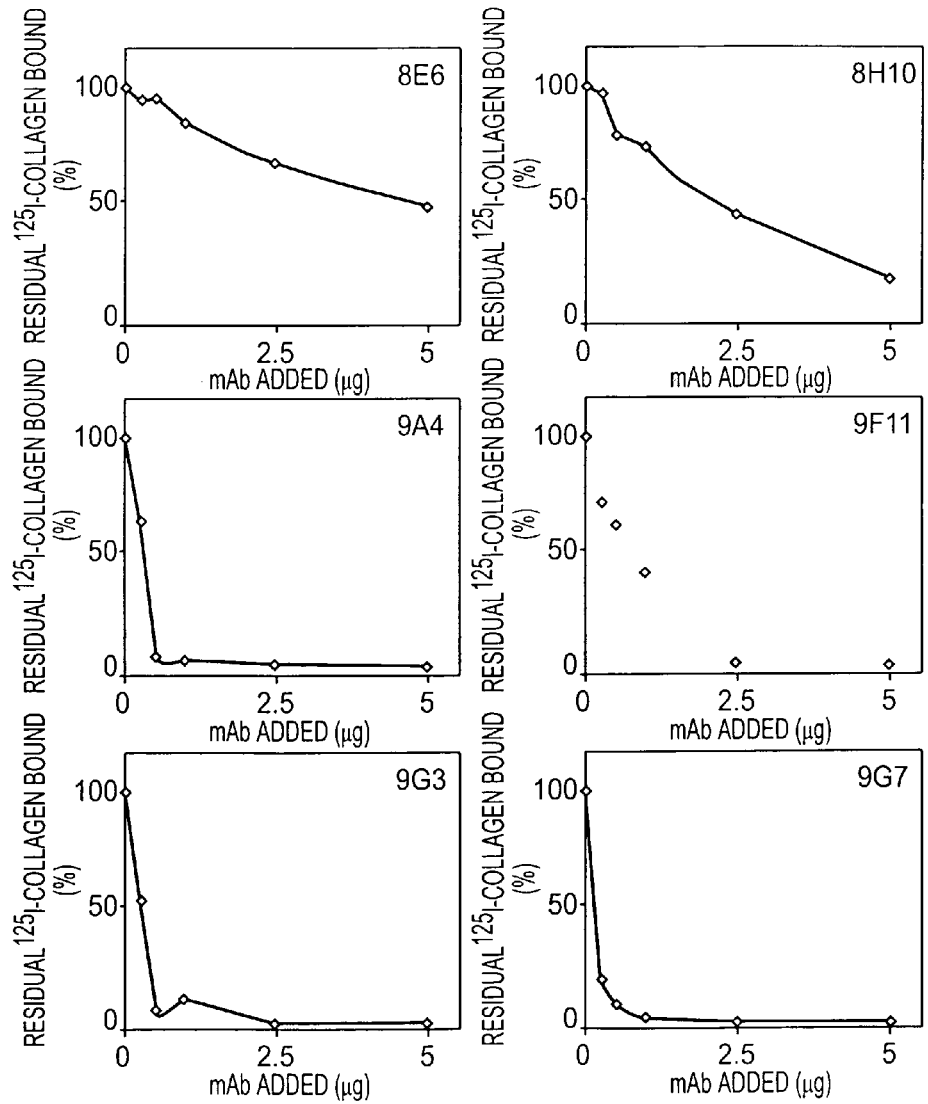
Figure 14C:
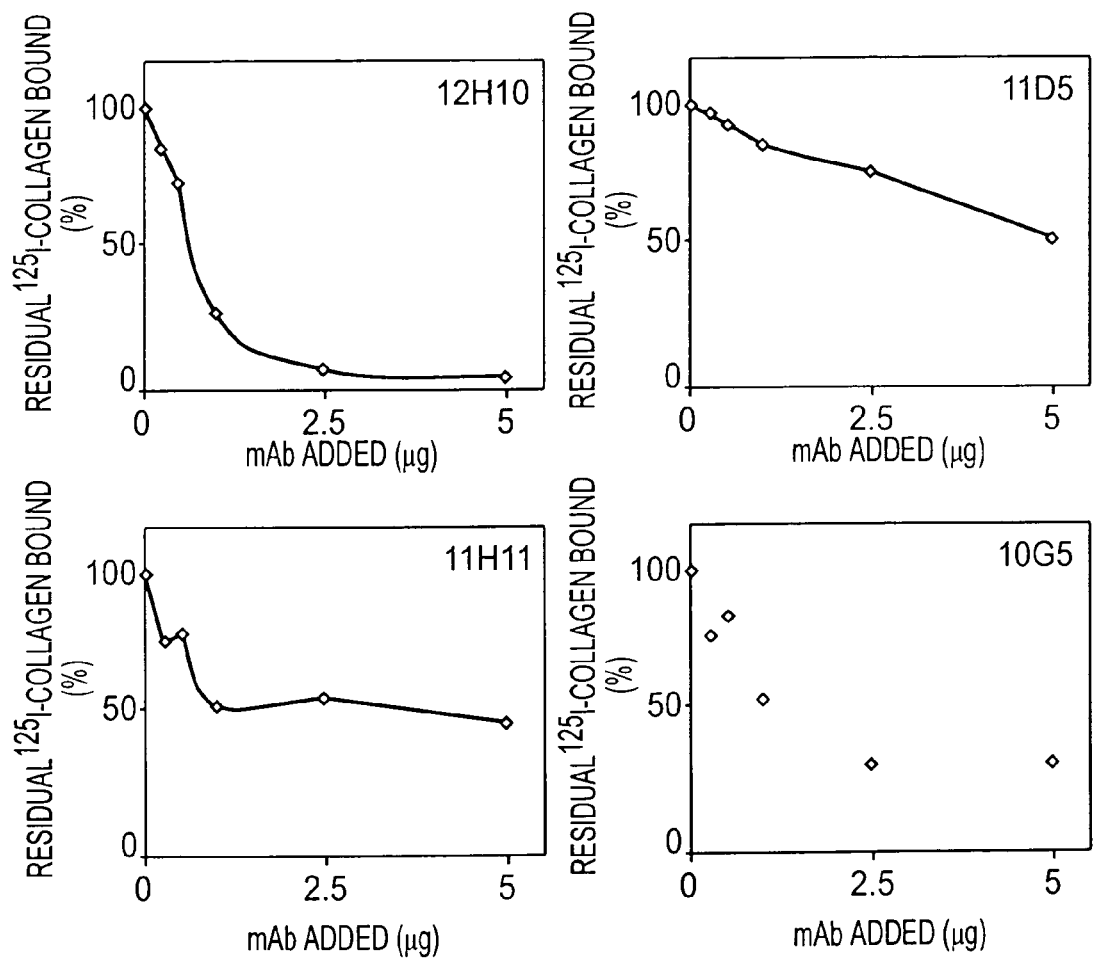

FIGS. 14A–14C. Displacement of S. aureus cells bound to immobilized collagen by mAbs generated against CNA19 (CBD 151–318).

Figure 15A:
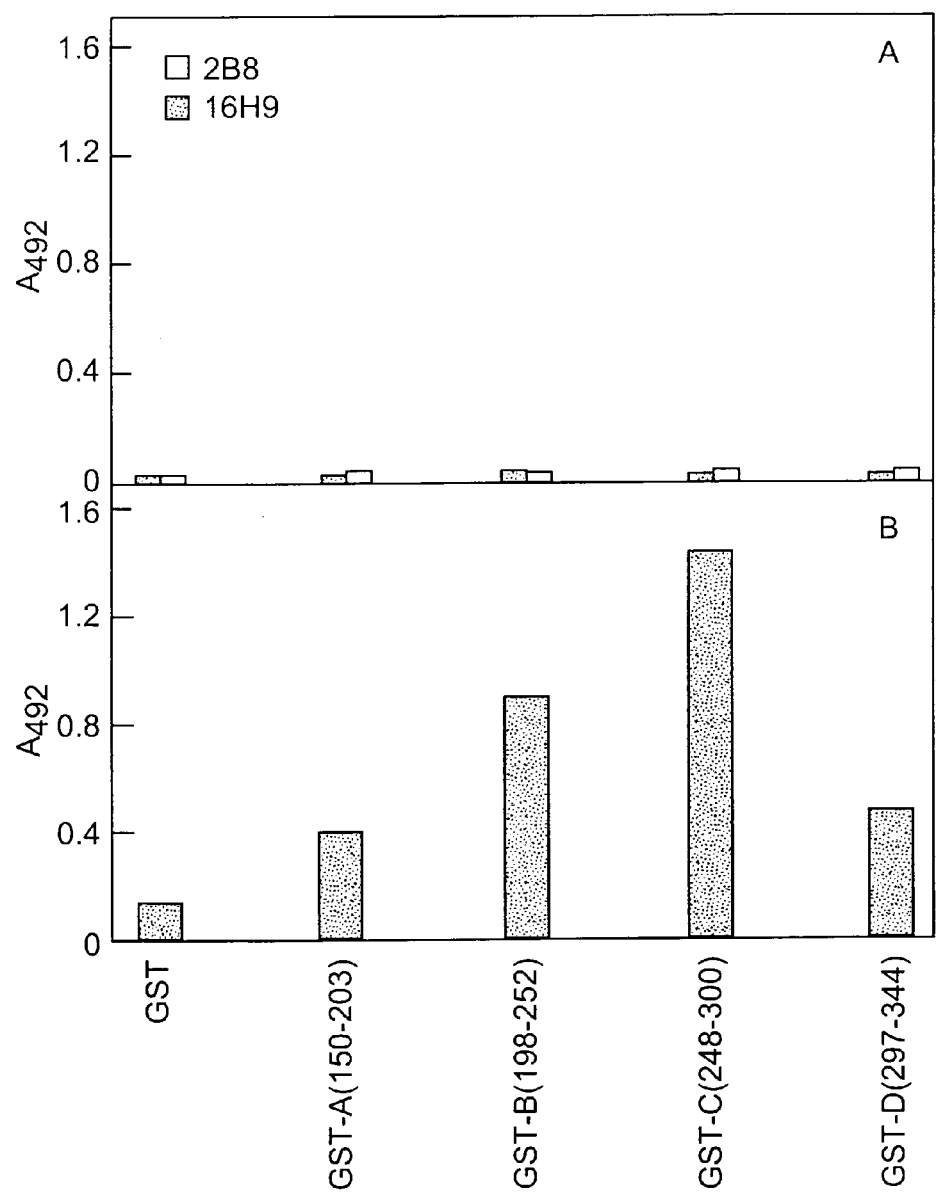

FIG. 15A. ELISA analysis of immobilized GST-CNA fusion protein derivatives with mAbs 2B8 and 16H9 and a polyclonal antibody raised against CBD (151–318).

Figure 15B:
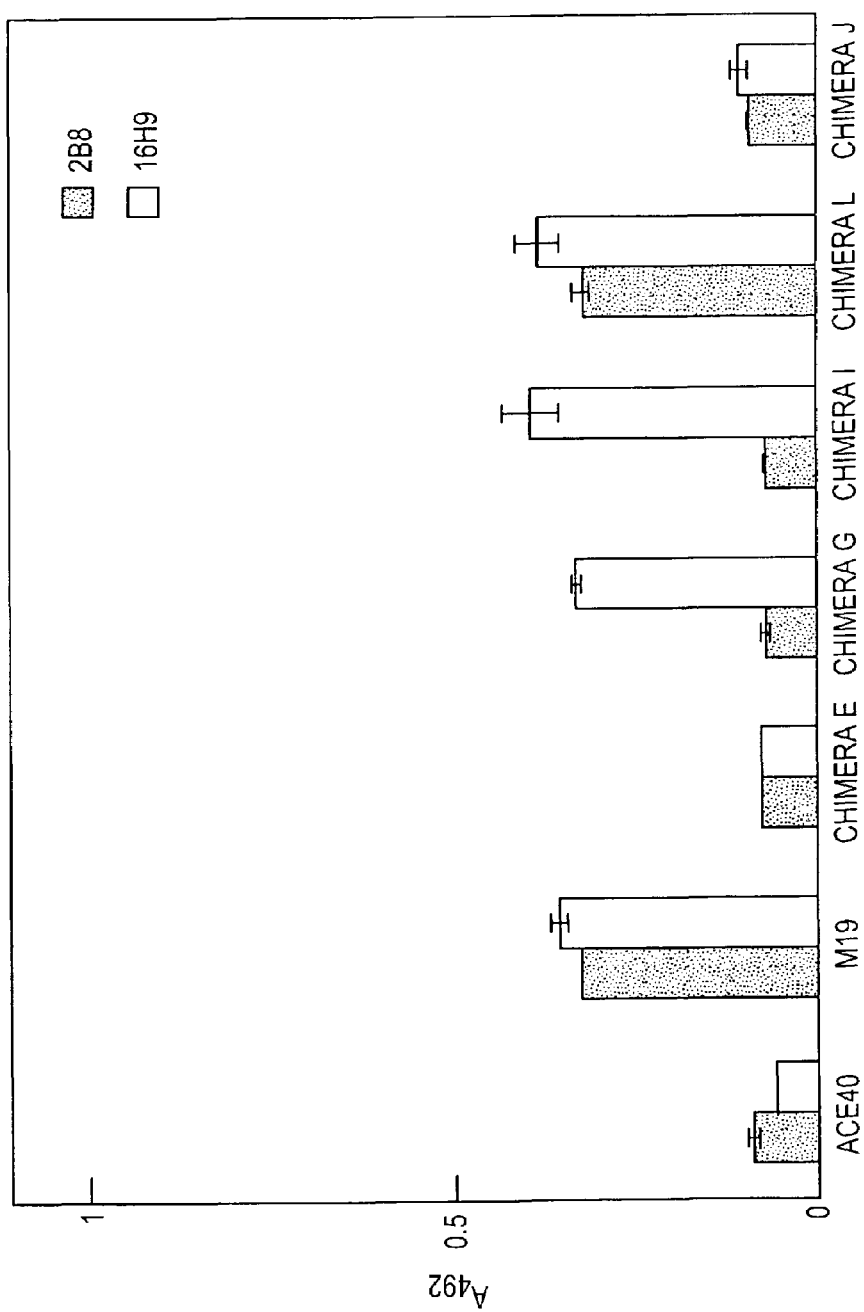

FIG. 15B. Mapping of epitope for mAbs 2B8 and 16H9 by using chimeras consisting of segments of ACE19 (174–319) and CNA19 (151–318).

FIG. 15C. Inhibitory activity of mAbs generated against CBD (30–529) on the collagen binding to S. aureus Cowan 1.

Figures 15D, 15E:
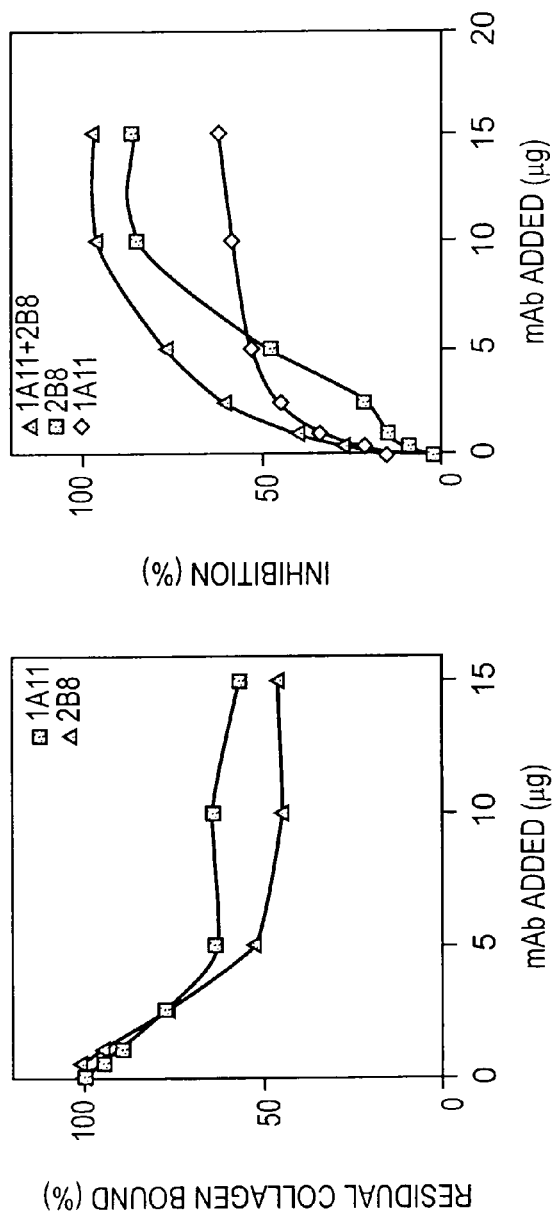
Figure 16A:
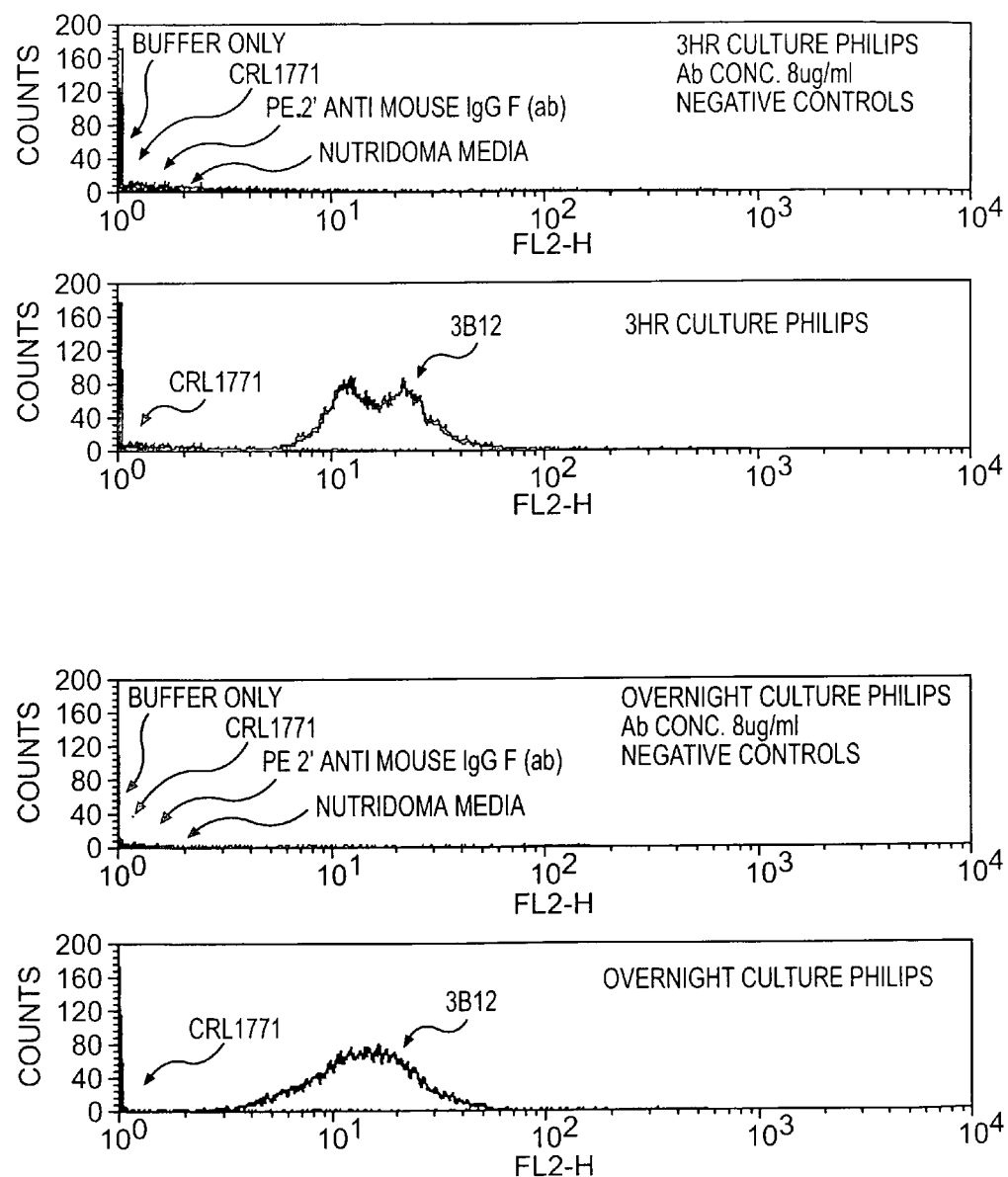
Figure 16B:
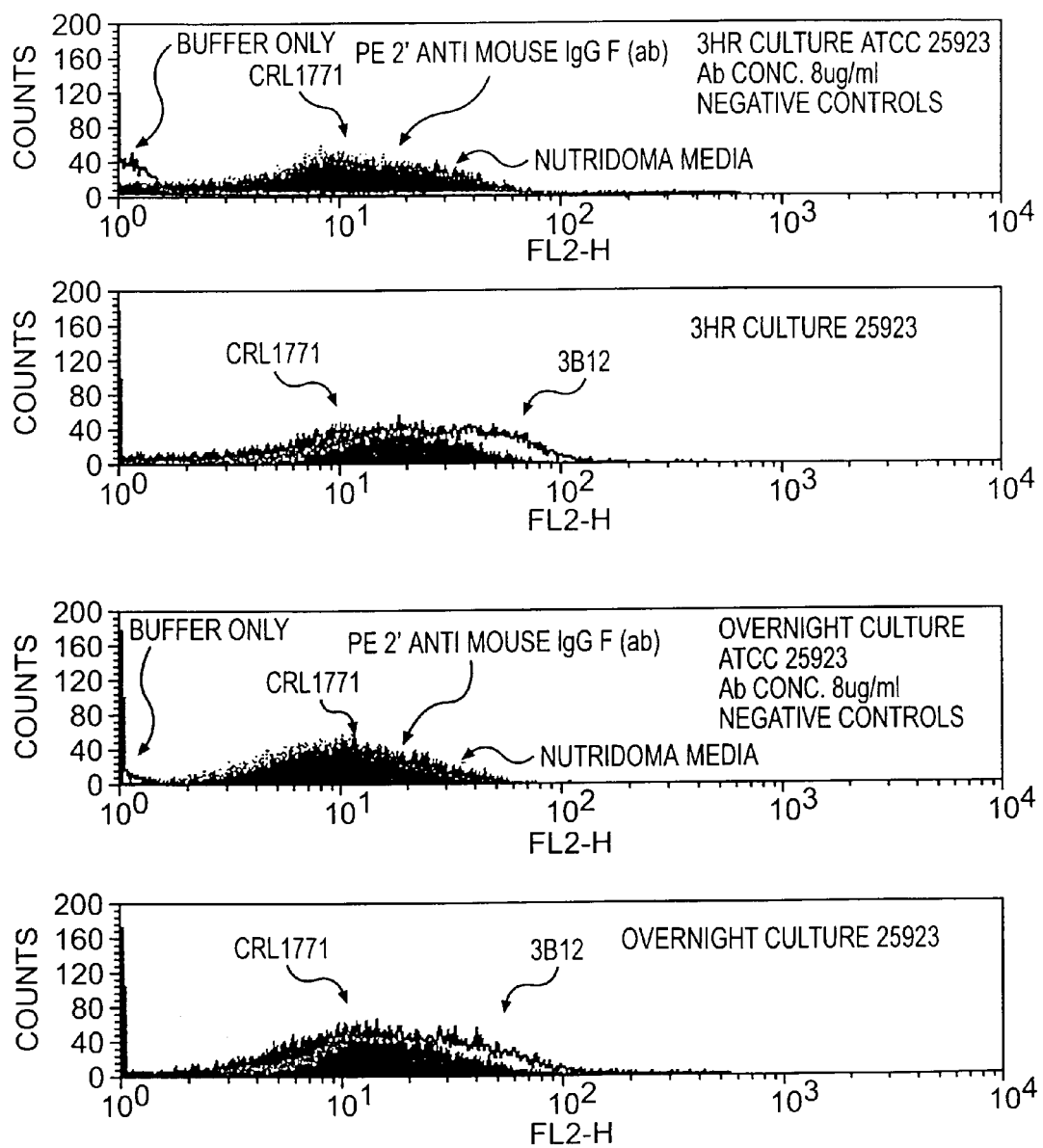
Figure 16C:
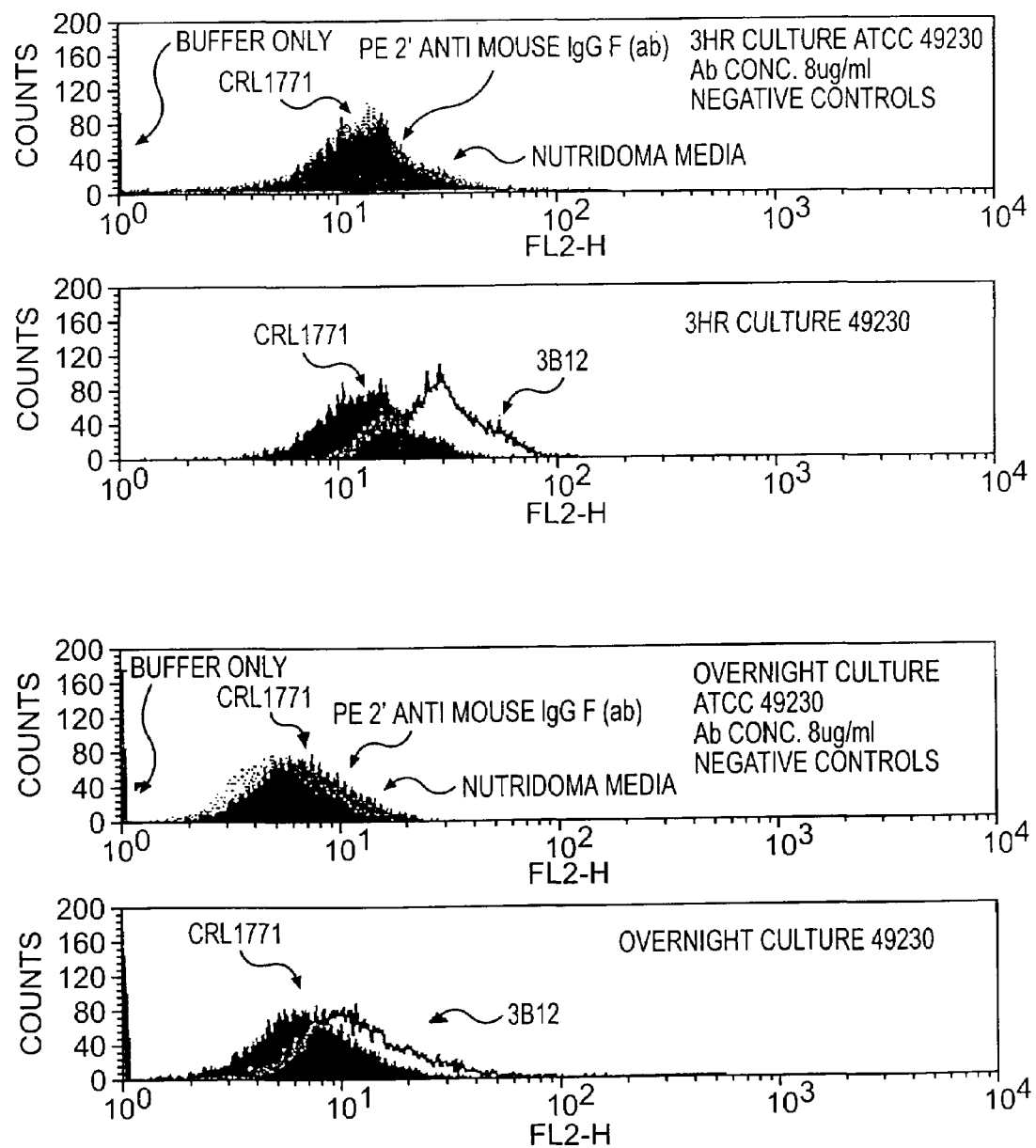
Figure 16D:
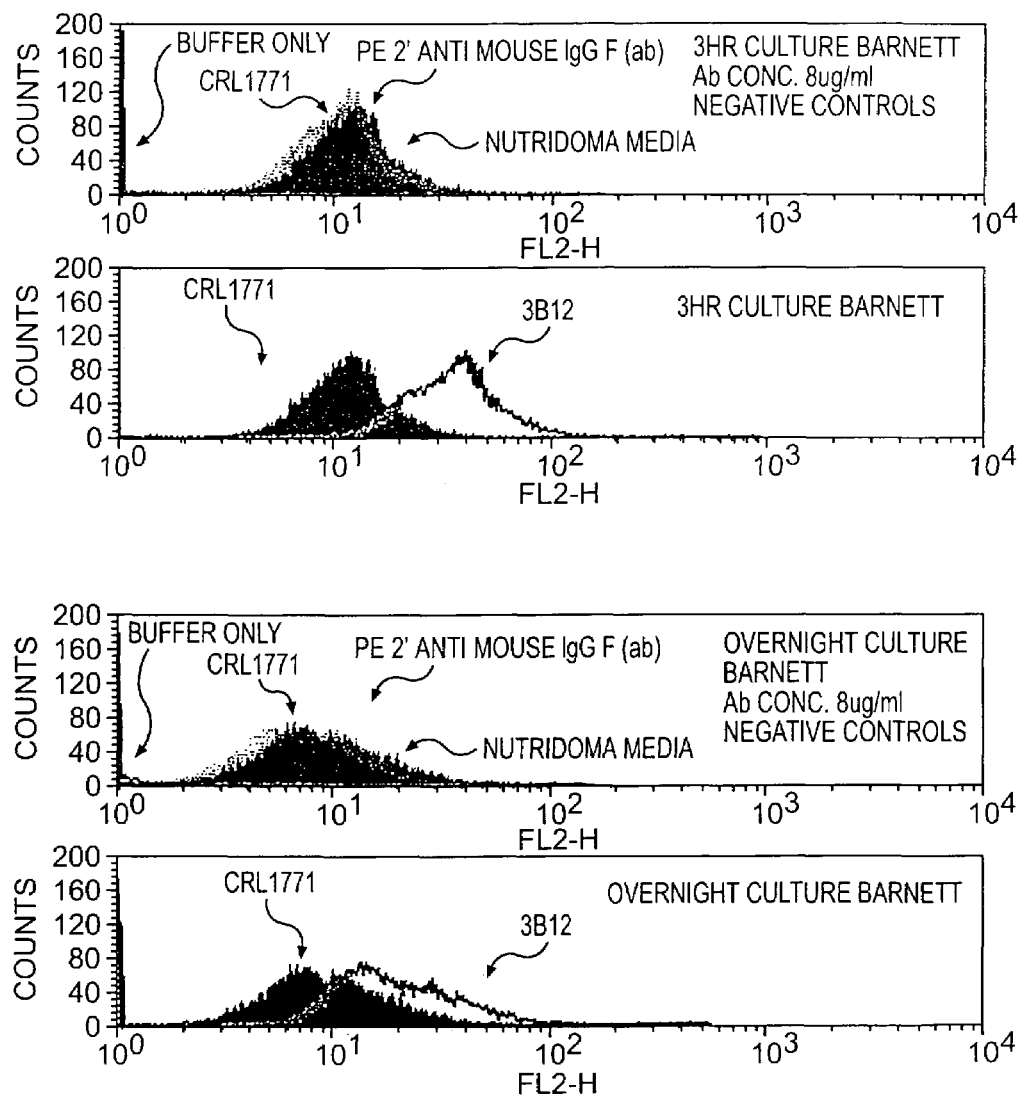

FIG. 15D. Displacement of $^{125}$I-collagen from S. aureus Cowan 1 by mAbs 1A 11 and 2B8.

FIG. 15E. Inhibition of $^{125}$I-collagen from S. aureus Cowan 1 by mAbs 1A11 and 2B8.

FIGS. 16A–16D. These are histogram representations which illustrate the staining profiles reflecting recognition of four different strains by monoclonal antibody designated 3B12 at 3 hr and overnight culture time points with each monoclonal.

DETAILED DESCRIPTION OF THE PREFERRED EMBODIMENTS

In accordance with the present invention, there is provided monoclonal antibodies to the CNA protein of S. aureus, as well as antibodies specific to the CNA19 region of the CNA collagen binding protein in staphylococcus bacteria which have been shown to be cross-reactive to both S. aureus and S. epidermidis. In addition, other antibodies generated to CNA19 have been shown to exhibit displacement behavior such that they may displace staph bacteria already bound to host cells.

The CNA protein in staphylococcal bacteria is a collagen-binding adhesin that allows the bacteria to target and bind to collagen in the extracellular matrix of host cells, and is thus a very important protein with regard to the colonization and multiplication of bacteria cells that can infect human and animal patients, and even colonize and affect medical instruments and prosthetic devices. Studies have actually shown that unlike many other proteins, the protein sequence of CNA, which is expressed by 60% of staphylococcal bacteria, is virtually identical across the great range of strains that express this protein, and there is little or no variation among the various strains with regard to CNA sequence. As a result, a monoclonal antibody generated to the CNA protein will be of tremendous value since unlike many other monoclonals which are very specific to a particular antigen and its sequence, a monoclonal antibody generated against the CNA protein will be extremely versatile in that it will recognize and protect against infection by a wide range of staphylococcal strains.

Accordingly, the present invention relates to an isolated and/or purified monoclonal antibody generated to the CNA protein or the CNA19 peptide which can be useful in methods of preventing and treating staphylococcal infection when used in amounts effective to prevent or treat such infections, and these monoclonal antibodies may be produced using, e.g., the method of Kohler and Milstein (29), or other suitable ways known in the field. Still other useful antibodies may be generated to larger segments of the A domain which will include the CNA19 region of the collagen binding domain, as further described below. Antisera prepared using monoclonal or polyclonal antibodies in accordance with the invention are also contemplated and may be prepared in a number of suitable ways as would be recognized by one skilled in the art.

In accordance with the invention, it is also contemplated that antibodies raised to the CNA19 peptide region of the CNA protein of S. aureus will be useful in the prevention and treatment of infection not only of S. aureus, but of S. epidermidis as well. With regard to antibodies to CNA19, these antibodies may be generated against natural isolated and purified CNA19, or, preferably, may be generated against recombinant CNA19. The CNA19 peptides against which antibodies are raised are preferably isolated from any of a variety of S. aureus strains, such as S. aureus strain Cowan I or strains such as those identified as 57, 72, 116, 175, 176, 180, 203, 205, 212 and 4046, which are clinical isolates from various countries around the world. Generally, it is preferred that the S. aureus strain utilized in accordance with the invention be one which is known to bind to collagen.

In accordance with the present invention, antibodies to the CNA19 motif of the CNA protein's collagen binding domain (or CBD 151–318) may be prepared in a number of suitable ways that would be well known in the art, such as the well-established Kohler and Milstein method (29) which can be utilized to generate monoclonal antibodies to CNA19. In this method, mice are injected intraperitoneally once a weeks for a prolonged period with a purified recombinant CNA19 domain, followed by a test of blood obtained from the immunized mice to determine reactivity to the purified CNA19 peptide. Following identification of mice reactive to CNA19, lymphocytes isolated from mouse spleens are fused to mouse myeloma cells to produce hybridomas positive for the antibodies against CNA19 which are then isolated and cultured, following by purification and isotyping.

In order to generate monoclonal antibodies in accordance with the invention, it is preferred that these be generated using recombinantly prepared CNA19 peptides in conventional methods well known in the art. For example, one such method employs the use of E. coli strain JM101 as a host and pQE-30 as an expression vector for cloning and expressing recombinant proteins and peptides. DNA preparation, purification, restriction digestion, agarose gel electrophoresis and ligation may be performed using standard methods, and the resulting recombinant CNA19 segments may be isolated and purified and then utilized to generate monoclonal antibodies in the manner described above.

In addition to monoclonal antibodies, the present invention also contemplates generating polyclonal antibodies from CNA19 as well. Such polyclonal antibodies may be generated in any of a number of suitable ways well known in the art, such as the introduction of a purified CNA19 peptide into a suitable animal host, followed by isolation and purification of the generated antibodies produced in the host animal.

Although production of antibodies using recombinant forms of the CNA19 motif is preferred, antibodies may be generated from natural isolated and purified CNA19 as well, and monoclonal or polyclonal antibodies can be generated using the natural CNA19 in the same manner as described above to obtain such antibodies. In addition, numerous other ways to generate the antibodies in accordance with the invention are possible, including expressing the whole CNA protein recombinantly and then isolating the CNA19 region from the isolated CNA protein. Still other conventional ways are available to generate the CNA19 antibodies of the present invention using recombinant or natural purified CNA19, as would be recognized by one skilled in the art.

As would be recognized by one skilled in the art, the antibodies of the present invention may also be formed into suitable pharmaceutical compositions for administration to a human or animal patient in order to treat or prevent an infection caused by staphylococcal bacteria such as S. aureus or S. epidermidis. Pharmaceutical compositions containing the antibodies of the present invention, or effective fragments thereof, may be formulated in combination with any suitable pharmaceutical vehicle, excipient or carrier that would commonly be used in this art, including such as saline, dextrose, water, glycerol, ethanol, other therapeutic compounds, and combinations thereof. As one skilled in this art would recognize, the particular vehicle, excipient or carrier used will vary depending on the patient and the patient's condition, and a variety of modes of administration would be suitable for the compositions of the invention, as would be recognized by one of ordinary skill in this art. Suitable methods of administration of any pharmaceutical composition disclosed in this application include, but are not limited to, topical, oral, anal, vaginal, intravenous, intraperitoneal, intramuscular, subcutaneous, intranasal and intradermal administration.

For topical administration, the composition is formulated in the form of an ointment, cream, gel, lotion, drops (such as eye drops and ear drops), or solution (such as mouthwash). Wound or surgical dressings, sutures and aerosols may be impregnated with the composition. The composition may contain conventional additives, such as preservatives, solvents to promote penetration, and emollients. Topical formulations may also contain conventional carriers such as cream or ointment bases, ethanol, or oleyl alcohol.

Additional forms of antibody compositions, and other information concerning compositions, methods and applications with regard to collagen binding proteins, are disclosed, for example, in U.S. patent application Ser. No. 08/856,253, filed May 14, 1997, U.S. patent application Ser. No. 09/494,297, filed Jan. 31, 2000, and in U.S. patent application Ser. No. 09/568,470, filed May 10, 2000, and the full specifications of these applications are incorporated herein by reference.

The antibody compositions of the present invention which are generated against the CNA19 or minimal collagen binding region of the CNA protein of S. aureus, yet which are also effective against S. epidermidis, may also be administered with a suitable adjuvant in an amount effective to enhance the immunogenic response against the conjugate. At this time, the only adjuvant widely used in humans has been alum (aluminum phosphate or aluminum hydroxide). Saponin and its purified component Quil A, Freund's complete adjuvant and other adjuvants used in research and veterinary applications have toxicities which limit their potential use in human vaccines. However, chemically defined preparations such as muramyl dipeptide, monophosphoryl lipid A, phospholipid conjugates such as those described by Goodman-Snitkoff et al. *J. Immunol.* 147: 410–415 (1991) and incorporated by reference herein, encapsulation of the conjugate within a proteoliposome as described by Miller et al., *J. Exp. Med.* 176:1739–1744 (1992) and incorporated by reference herein, and encapsulation of the protein in lipid vesicles such as Novasome™ lipid vesicles (Micro Vescular Systems, Inc., Nashua, N.H.) may also be useful.

In any event, the antibody compositions of the present invention will thus be useful for interfering with, modulating, inhibiting binding interactions between staphylococcal bacteria and collagen on host cells, or in displacing staphylococcal bacteria which has become bound to the collagen on host cells.

In accordance with the present invention, methods are provided for preventing or treating a staphylococcal infection which comprise administering an effective amount of an antibody to CNA19 as described above in amounts effective to treat or prevent the infection. As also indicated above, the CNA19 antibodies have been observed to exhibit an ability to displace *S. aureus* bacteria that are bound to collagen, such as the collagen in the extracellular matrix of host cells, and thus one of the advantageous aspects of the present invention is the provision of a method and a composition which can be utilized to fight a standing infection of staphylococcal bacteria such as *S. aureus* and *S. epidermidis* because the CNA19 antibodies of the present invention will displace the bacteria from collagen in the host cells. Accordingly, in accordance with the invention, administration of the antibodies of the present invention in any of the conventional ways described above (e.g., topical, parenteral, intramuscular, etc.) will be useful in displacing staphylococcal infections in a manner not heretofore possible, and will thus provide an extremely useful method of treating staphylococcal infections in human or animal patients. By effective amount is meant that level of antibody titer that will be sufficient to either inhibit binding of staph bacteria to host cells, or, in the case of a prior infection, that amount that will be sufficient to displace bacteria from the host cells so as to treat the infection. As would be recognized by one of ordinary skill in this art, the level of antibody titer needed to be effective in treating or preventing staphylococcal infection will vary depending on the nature and condition of the patient, and/or the severity of the pre-existing staphylococcal infection.

The isolated antibodies in accordance with the present invention which show displacing activity to binding sites such that they will displace proteins already bound to such sites can thus be administered to humans or animals, either alone or in combination with an adjuvant, in a number of suitable ways conventionally used to treat or prevent a staphylococcal infection.

In addition to the use of antibodies to CNA19 as described above, the present invention contemplates the use of these antibodies in a variety of ways, including the detection of the presence of Staphylococcal bacteria such as *S. aureus* or *S. epidermidis* and thus using antibodies to diagnose a staph infection, whether in a patient or on medical equipment which may also become infected. In accordance with the invention, a preferred method of detecting the presence of staph infections involves the steps of obtaining a sample suspected of being infected by one or more staphylococcal bacteria species or strains, such as a sample taken from an individual, for example, from one's blood, saliva, tissues, bone, muscle, cartilage, or skin. The cells can then be lysed, and the DNA extracted, precipitated and amplified. Following isolation of the sample, diagnostic assays utilizing the antibodies of the present invention may be carried out to detect the present of staph bacteria, including *S. aureus* or *S. epidermidis*, and such assay techniques for determining such presence in a sample are well known to those skilled in the art and include methods such as radioimmunoassay, Western blot analysis and ELISA assays.

Accordingly, antibodies in accordance with the invention may be used for the specific detection of staphylococcal collagen-binding proteins, for the prevention of infection from staph bacteria, for the treatment of an ongoing infection, or for use as research tools. The term "antibodies" as used herein includes monoclonal, polyclonal, chimeric, single chain, bispecific, simianized, and humanized or primatized antibodies as well as Fab fragments, including the products of an Fab immunoglobulin expression library. Generation of any of these types of antibodies or antibody fragments is well known to those skilled in the art. In the present case, specific polyclonal antiserum against CNA19 has been generated which reacts with CNA19 in Western immunoblots and ELISA assays and interferes with binding to collagen.

Any of the above described antibodies may be labeled directly with a detectable label for identification and quantification of staph bacteria. Labels for use in immunoassays are generally known to those skilled in the art and include enzymes, radioisotopes, and fluorescent, luminescent and chromogenic substances, including colored particles such as colloidal gold or latex beads. Suitable immunoassays include enzyme-linked immunosorbent assays (ELISA).

Alternatively, the antibody may be labeled indirectly by reaction with labeled substances that have an affinity for immunoglobulin. The antibody may be conjugated with a second substance and detected with a labeled third substance having an affinity for the second substance conjugated to the antibody. For example, the antibody may be conjugated to biotin and the antibody-biotin conjugate detected using labeled avidin or streptavidin. Similarly, the antibody may be conjugated to a hapten and the antibody-hapten conjugate detected using labeled anti-hapten antibody. These and other methods of labeling antibodies and assay conjugates are well known to those skilled in the art.

Antibodies to the collagen-binding protein domain CNA19 may also be used in production facilities or laboratories to isolate additional quantities of the proteins, such as by affinity chromatography. For example, the antibodies of the invention may also be utilized to isolate additional amounts of collagen.

The isolated antibodies of the present invention, or active fragments thereof, may also be utilized in the development of vaccines for passive immunization against staph infections. Further, when administered as pharmaceutical composition to a wound or used to coat medical devices or polymeric biomaterials in vitro and in vivo, the antibodies of the present invention, since they exhibit displacing behavior, are especially useful in those cases where there is a previous staph infection already present since these antibodies will function to displace this bacterial infection. In addition, the antibody may be modified as necessary so that, in certain instances, it is less immunogenic in the patient to whom it is administered. For example, if the patient is a human, the antibody may be "humanized" by transplanting the complimentarity determining regions of the hybridoma-derived antibody into a human monoclonal antibody as described, e.g., by Jones et al., *Nature* 321:522–525 (1986) or Tempest et al. *Biotechnology* 9:266–273 (1991).

Medical devices or polymeric biomaterials to be coated with the antibodies, proteins and active fragments described herein include, but are not limited to, staples, sutures, replacement heart valves, cardiac assist devices, hard and soft contact lenses, intraocular lens implants (anterior chamber or posterior chamber), other implants such as corneal inlays, kerato-prostheses, vascular stents, epikeratophalia devices, glaucoma shunts, retinal staples, scleral buckles, dental prostheses, thyroplastic devices, laryngoplastic devices, vascular grafts, soft and hard tissue prostheses including, but not limited to, pumps, electrical devices including stimulators and recorders, auditory prostheses, pacemakers, artificial larynx, dental implants, mammary implants, penile implants, cranio/facial tendons, artificial joints, tendons, ligaments, menisci, and disks, artificial bones, artificial organs including artificial pancreas, artificial hearts, artificial limbs, and heart valves; stents, wires, guide wires, intravenous and central venous catheters, laser and balloon angioplasty devices, vascular and heart devices (tubes, catheters, balloons), ventricular assists, blood dialysis components, blood oxygenators, urethral/ureteral/urinary devices (Foley catheters, stents, tubes and balloons), airway catheters (endotracheal and tracheostomy tubes and cuffs), enteral feeding tubes (including nasogastric, intragastric and jejunal tubes), wound drainage tubes, tubes used to drain the body cavities such as the pleural, peritoneal, cranial, and pericardial cavities, blood bags, test tubes, blood collection tubes, vacutainers, syringes, needles, pipettes, pipette tips, and blood tubing.

It will be understood by those skilled in the art that the term "coated" or "coating", as used herein, means to apply the antibody or active fragment, or pharmaceutical composition derived therefrom, to a surface of the device, preferably an outer surface that would be exposed to streptococcal bacterial infection. The surface of the device need not be entirely covered by the protein, antibody or active fragment.

In a preferred embodiment, the antibodies may also be used as a passive vaccine which will be useful in providing suitable antibodies to treat or prevent a staphylococcal infection. As would be recognized by one skilled in this art, a vaccine may be packaged for administration in a number of suitable ways, such as by parenteral (i.e., intramuscular, intradermal or subcutaneous) administration or nasopharyngeal (i.e., intranasal) administration. It is generally preferred that the vaccine be injected intramuscularly into the deltoid muscle, however, the particular mode of administration will depend on the nature of the bacterial infection to be dealt with and the condition of the patient. The vaccine is preferably combined with a pharmaceutically acceptable carrier to facilitate administration, and the carrier is usually water or a buffered saline, with or without a preservative. The vaccine may be lyophilized for resuspension at the time of administration or in solution.

The preferred dose for administration of an antibody composition in accordance with the present invention is that amount will be effective in preventing of treating a staphylococcal infection, and one would readily recognize that this amount will vary greatly depending on the nature of the infection and the condition of a patient. As indicated above, an "effective amount" of antibody or pharmaceutical agent to be used in accordance with the invention is intended to mean a nontoxic but sufficient amount of the agent, such that the desired prophylactic or therapeutic effect is produced. As will be pointed out below, the exact amount of the antibody or a particular agent that is required will vary from subject to subject, depending on the species, age, and general condition of the subject, the severity of the condition being treated, the particular carrier or adjuvant being used and its mode of administration, and the like. Accordingly, the "effective amount" of any particular antibody composition will vary based on the particular circumstances.

However, an appropriate effective amount may be determined in each case of application by one of ordinary skill in the art using only routine experimentation. In this regard, it is generally preferred that compositions in accordance with the invention contain from about 0.5 to 75 mg/kg of a CNA19 antibody in accordance with the invention, with about 5 to 30 mg/kg range being a more common desired range of level of antibody. Based on this range, equivalent dosages for heavier body weights can be determined. The dose should be adjusted to suit the individual to whom the composition is administered and will vary with age, weight and metabolism of the individual. The compositions may additionally contain stabilizers or pharmaceutically acceptable preservatives, such as thimerosal (ethyl(2-mercaptobenzoate-S)mercury sodium salt) (Sigma Chemical Company, St. Louis, Mo.).

When used with suitable labels or other appropriate detectable biomolecule or chemicals, the monoclonal antibodies described herein are useful for purposes such as in vivo and in vitro diagnosis of staphylococcal infections or detection of staphylococcal bacteria. Laboratory research may also be facilitated through use of such antibodies. Various types of labels and methods of conjugating the labels to the antibodies of the invention are well known to those skilled in the art, such as the ones set forth below.

For example, the antibody can be conjugated to a radiolabel such as, but not restricted to, $^{32}P$, $^{3}H$, $^{14}C$, $^{35}S$, $^{125}I$, or $^{131}I$. Detection of a label can be by methods such as scintillation counting, gamma ray spectrometry or autoradiography. Bioluminescent labels, such as derivatives of firefly luciferin, are also useful. The bioluminescent substance is covalently bound to the protein by conventional methods, and the labeled protein is detected when an enzyme, such as luciferase, catalyzes a reaction with ATP causing the bioluminescent molecule to emit photons of light. Fluorogens may also be used to label proteins. Examples of fluorogens include fluorescein and derivatives, phycoerythrin, allo-phycocyanin, phycocyanin, rhodamine, and Texas Red. The fluorogens are generally detected by a fluorescence detector.

The location of a ligand in cells can be determined by labeling an antibody as described above and detecting the label in accordance with methods well known to those skilled in the art, such as immunofluorescence microscopy using procedures such as those described by Warren and Nelson (*Mol. Cell. Biol.*, 7: 1326–1337, 1987).

As indicated above, the monoclonal antibodies of the present invention, or active portions or fragments thereof, are particularly useful for interfering with the initial physical interaction between a staphylococcal pathogen responsible for infection and a mammalian host, such as the adhesion of the bacteria to mammalian extracellular matrix proteins such as collagen, and this interference with the physical interaction may be useful both in treating patients and in preventing or reducing bacteria infection on in-dwelling medical devices to make them safer for use.

In another embodiment of the present invention, a kit which may be useful in isolating and identifying staphylococcal bacteria and infection is provided which comprises the antibodies of the present invention in a suitable form, such as lyophilized in a single vessel which then becomes active by addition of an aqueous sample suspected of containing the staphylococcal bacteria. Such a kit will typically include a suitable container for housing the antibodies in a suitable form along with a suitable immunodetection reagent which will allow identification of complexes binding to the CNA19 antibodies of the invention. For example, the immunodetection reagent may comprise a suitable detectable signal or label, such as a biotin or enzyme that produces a detectable color, etc., which normally may be linked to the antibody or which can be utilized in other suitable ways so as to provide a detectable result when the antibody binds to the antigen.

In short, the antibodies of the present invention which bind to the CNA19 region of a collagen binding protein of staphylococcal bacteria, and which can displace the attachment of staphylococcal bacteria of more than one species to a host cell, are thus extremely useful in treating or preventing staphylococcal infections in human and animal patients and in medical or other in-dwelling devices.

In addition, in accordance with the present invention, there is provided a method of identifying and isolating antibodies which exhibit displacing activity and which can be utilized to displace a bacteria that has become bound to a given site on a host cell. In the preferred method in accordance with the invention, a medium comprising a known site for bacterial binding attachment, such as surface protein of the extracellular matrix of a host cell (e.g., collagen, laminin, etc.), is first labeled with an appropriate detectable label, such as a radioactive label like $^{125}$I. Next, the labeled binding site medium, such as labeled collagen or other protein, which may be in immobilized form, is placed in contact with the appropriate bacteria known to bind to it, such as Staphylococcal bacteria including S. aureus and S. epidermidis, and left in contact with the bacteria for a time sufficient so that the bacteria will bind to the protein or other appropriate material from a binding site. Followed sufficient time for binding, the bacteria bound to the detectable label are preferably harvested, and then placed in a suitable medium wherein an antibody suspected of having displacement activity against the particular bacteria at that binding site can be introduced to the labeled bacteria. Following this step, it will be a routine matter to determine which of the bacteria have been displaced from their binding sites, or the proteins which make up those binding sites, and thus identify and isolate those antibodies which have been able to effect such displacement. This method may be used with surface proteins, or other proteins or materials to which it is known that bacteria will attach, and in each case, an antibody which recognizes the binding medium can be tested to determine its displacing activity for bacteria attached to the binding medium. Antibodies which are identified and/or isolated using the present method, such as the CNA19 antibody which exhibits such displacement activity, thus constitute an additional part of the present invention

EXAMPLES

The following examples are provided which exemplify aspects of the preferred embodiments of the present invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Generation of Monoclonal Antibodies and Demonstration of Displacement Effects and Cross-Reactivity Bacterial strains, plasmids and culture conditions—Escherichia coli strain JM101 was used as a host and pQE-30 (Qiagen Inc., Chatsworth, Calif.) as an expression vector for cloning and expressing recombinant proteins. Staphylococcus aureus strain Cowan I was a clinical isolate from the Instituto Seroterapico Milanese (Milan, Italy) (18). S. aureus strains 57, 72, 116, 175, 176, 180, 203, 205, 212, and 4046 were clinical isolates from China, Europe, Hong Kong, Singapore and the United States. All these S. aureus isolates bind collagen (data not shown). E. coli strains were grown in Lennox L Broth (LB) (SIGMA, St. Louis, Mo. 63178) or on LB agar at 37° C. overnight with antibiotics when appropriate. Staphylococci were grown in Brain Heart Infusion (BHI) (DIFCO, Detroit, Mich. 48232-7058) broth or on BHI agar at 37° C. overnight.

Generation of monoclonal antibodies—Monoclonal antibodies against CNA19 were produced essentially as described by Köhler and Milstein (29) with minor modifications. BALB/c mice were injected intraperitoneally five times at 1-week intervals with 50 μg of the purified recombinant protein. The antigen was emulsified with an equal volume of complete Freund's adjuvant for the first immunization, followed by three injections in incomplete adjuvant. The mice were bled and the sera were tested for reactivity to the purified CNA19 using ELISA and Western blot. For the final immunization the antigen was given in saline. Three days after, the lymphocytes isolated from spleens were fused with Spe/0 Ag.14 mouse myeloma cells at a ratio of 5:1 using 50% polyethyleneglycol 4000. The suspended cells were first grown and selected in high glucose DMEM/RPMI 1640 (1:1) medium (Sigma, St. Louis, Mo.) containing 2% hypoxantin/aminopterin/thymidine (HAT) (Sigma), 2% glutamine, 2% penicillin and streptomycin. After 1 week, the HAT medium was progressively replaced by culturing cloned hybridomas in a serum-free medium consisting of DMEM/RPMI 1640 supplemented with 1% (v/v) Nutridoma-SR (Boehringer Mannheim, Mannheim, Germany) and antibiotics. Supernatants of the cell cultures were screened by ELISA on day 10, and hybridomas positive for the antibodies against CNA19 were subcultured to a density of 1 cell per well by limiting dilution and further characterized by ELISA and Western blot.

16H9 was an mAb raised against CNA55 using the same method. 7E8 was an anti-His tag mAb generated using the same procedure.

Antibody purification and isotyping—Supernatants of hybridoma cells were collected and centrifuged. The antibodies were purified by using ammonium sulfate precipitation of the supernatant, followed by affinity chromatography on Protein A/G—Sepharose columns according to the recommendations of the manufacturer (Amersham Pharmacia Biotech).

Isotyping of the produced monoclonal antibodies (mAbs) was performed using a Mouse-Typer sub-isotyping kit (Bio-rad, Richmond, Calif.).

Routine DNA manipulation and transformation of *E. coli*—DNA preparation, purification, restriction digestion, agarose gel electrophoresis and ligation were performed using standard methods (30) or following the manufacturer's instructions unless otherwise stated. Restriction enzymes, T4 DNA ligase and calf intestine alkaline phosphatase were from Life Technologies, GIBCO BRL (Gaithersburg, Md. 20884-9980). DNA for sequencing was prepared using the QIAprep Spin Miniprep kit (Qiagen). Routine preparation of *E. coli* competent cells and transformation of DNA into *E. coli* were performed by a one-step procedure (31).

Cloning of ace19—The amino acid sequences of CNA55 and ACE40 were compared using ClustalW with the default parameters. The region from amino acid 152–318 in ACE40 was used to construct ACE19. Primers were designed to PCR amplify the corresponding nucleotide sequence (Table 1A) using Pfu DNA polymerase (Stratagene, La Jolla, Calif. 92037) according to manufacturer's instructions. The primers were designed such that the PCR product contained a BamHI site at its 5' end and a stop codon followed by a SalI site at its 3' end. The PCR product was digested with BamHI and SalI and purified. It was then ligated to BamHI and SalI digested and dephosphatased pQE-30 (Qiagen, Chatsworth, Calif.). The ligation mixture was transformed into *E. coli* JM101 and the cells were incubated on LB agar plates supplemented with 50 µg/ml ampicillin at 37° C. overnight to select for transformants. The construct was confirmed by restriction enzyme digestions and further verified by DNA sequencing.

Generation of constructs containing chimeric sequences between ACE19 and CNA19—Overlapping PCR strategy was used for the construction. Primers that span each corresponding junction region between ACE19 and CNA19 were designed (Table 1A). PCR reactions were carried out using the proper combination of primers and templates (Table 1B). The construction of chimera L was used as an example. Briefly, the primer to the 5' end of ace19, ACE19 5', and ACE19I which spans the junction region between ACE19 and CNA19 were used to amplify the N-terminal quarter segment from ACE19. The corresponding CNA19 primers, CNA19I and CNA19 3' were used to amplify the C-terminal three-quarters segment from CNA19. PCR reactions were as described above for the cloning of ACE19. After the reactions, 1 µl of a 5-fold dilution of each reaction were mixed and used as templates for the second round PCR with primers ACE19 5' and CNA19 3'. Each construct was confirmed by DNA sequencing.

Expression of recombinant proteins in *E. coli* and protein purification—Protein expression and purification were described previously (14,21). Briefly, one liter of LB (supplemented with 50 µg/ml ampicillin) was inoculated with 40 ml of an overnight culture of a recombinant *E. coli* strain and grown at 37° C. for 3 hours. Isopropyl-β-D-thiogalactoside was added and the culture was grown for another 3 hours to allow protein expression. Bacteria were harvested by centrifugation, the cell pellets were resuspended in phosphate-buffered saline (PBS), pH 7.4, and stored at −80° C.

The pellets were thawed and lysed in a French press. The cell debris was removed by centrifugation and the supernatant filtered through a 0.45-µm membrane. The supernatant was applied to a 5 ml $Ni^{2+}$-charged HiTrap chelating column (Amersham Pharmacia Biotech) and bound protein was eluted with a 200-ml linear gradient of 0–200 mM imidazole in 4 mM Tris-HCl, 100 mM NaCl, (pH 7.9), at a flow rate of 5 ml/min. Fractions corresponding to each recombinant protein, as determined by SDS-PAGE, were pooled and dialyzed against HBS buffer (10 mM HEPES, 150 mM NaCl, pH7.4) containing 3.4 mM EDTA. Protein concentration was measured on a Beckman DU-70 UV-visible spectrophotometer at $\lambda_{280-315}$. Molar extinction coefficient of each protein was calculated using values of Pace et al. (32).

Circular dichroism (CD)—Far-UV CD was performed as described (33) using a Jasco J720 spectropolarimeter. All sample concentrations were either at 5 or 10 µM in 0.5% PBS. Spectra were recorded at room temperature in cylindrical 0.5 mm path length cuvettes.

Enzyme-linked immunosorbent assay (ELISA).—Microtiter wells were coated overnight at 4° C. with 100 µl of 10 µg/ml of each recombinant protein in 50 mM sodium carbonate, pH 9.5. To block additional protein binding sites, the wells were treated for 1 h at 22° C. with 200 µl of PBS containing 2% bovine serum albumin (BSA) and then washed five times with PBST (PBS with 0.1% Tween 20). Indicated amounts of each mAb dissolved in 100 µl PBS with 2% BSA were added to the wells and incubated for 2 h at 22° C. Plates were then extensively washed with PBST and incubated for 1 h with a rabbit anti-mouse IgG conjugated to horseradish peroxidase (1:500 dilution) (Dako, Gostrup, Denmark). After washing, binding was quantitated using the substrate o-phenylenediamine dihydrochloride (Sigma) and measuring the absorbance at 492 nm in a microplate reader (Bio-Rad). The concentration required for half-maximal binding of the antibody to CNA19 was used to calculate the apparent $K_D$ of each mAb.

Iodination of collagen—Type II collagen was prepared from bovine nasal septum as described by Strawich and Nimmi (34). Carrier-free $^{125}I$ (15 mCi/µg) was from Amersham Pharmacia biotech. Collagen was labeled using the iodogen coated-tube technique as recommended by the manufacturer (Pierce, Rockford, Ill.). The specific activity of the radiolabeled ligand was estimated to be $4\times10^6$ cpm/µg.

Inhibition of the collagen binding of CNA19 by the mAbs.—Microtiter wells were coated with CNA19 as in ELISA described above and then incubated with $^{125}I$-collagen ($8\times10^4$ cpm) in the presence of certain amount of each mAb for 1 h. After extensive washing, the radioactivity in each well was measured in a γ counter. The amount of radioactivity in each well was compared to that of the well with no mAb. All experiments were done in duplicates.

Binding of collagen to staphylococci and the inhibition and displacement effects of the mAbs—Binding of $^{125}I$-labeled collagen to *S. aureus* cells was quantitated as described previously (35). Briefly, $5\times10^8$ *S. aureus* Cowan I cells were incubated with $5\times10^4$ cpm of $^{125}I$-collagen in 0.5 ml of PBS containing 0.1% BSA and 0.1% Tween 80. The mixture was rotated in an end-over-end mixer for 1 h at 22° C. The reaction was stopped by the addition of 2.5 ml of ice-cold PBS containing 0.1% Tween 80, and the tubes were centrifuged at 1400×g for 10 min. After aspiration of the supernatant, the pellet was analyzed for radioactivity in a γ counter. Radioactivity recovered in the tubes incubated in the absence of bacteria (400–600 cpm) was subtracted from that of the samples containing bacteria. Samples were run in duplicate.

To examine the inhibition effect of the mAbs on the binding to soluble collagen, bacteria were pre-incubated with increasing amounts of each mAbs for 1 h before the addition of $^{125}$I-collagen, and processed as above.

To examine the displacement effect of the mAbs on collagen binding, bacteria were pre-incubated with $^{125}$I-collagen for 1 hour. After centrifugation, the supernatant was removed, the bacteria-collagen pellet was washed and resuspended in PBS containing 0.1% BSA and 0.1% Tween 80 with certain amounts of each mAb, and incubated for another hour. The amount of residual collagen bound to bacteria was determined as above.

Adherence of S. aureus cells to immobilized collagen substrates and the inhibition and displacement effects of the mAbs.—Microtiter wells were incubated with 100 µl of 10 µg/ml of type II collagen in 50 mM sodium carbonate, pH 9.5, overnight at 4° C., and then subjected to blocking with 200 µl of 2% BSA for 1 h at 22° C. After washing with PBST, the wells were incubated with 100 µl of a suspension of Cowan I ($1 \times 10^7$ cells/ml) at 22° C. for 2 h, and then washed extensively with PBST. Adherent cells were detected by incubation of the wells for 1 h with 100 µl of a horseradish peroxidase-conjugated rabbit anti-mouse IgG (1:500 dilution). Color development and measurement was as described above.

To study the inhibition of bacterial adherence to immobilized collagen by the mAbs, cells were pre-incubated for 30 min with the indicated amounts of each antibody. The cells were transferred to the collagen-coated wells, incubated for 2 h and processed as above.

In the displacement experiments, bacteria were first incubated with collagen coated wells and then incubated with increasing concentrations of the indicated mAbs for 2 h. The bacteria remained attached to collagen were detected by the addition of horseradish peroxidase-conjugated rabbit anti-mouse IgG as described above. In one experiment, the bacteria were also detected using horseradish peroxidase-conjugated goat anti-rabbit IgG, as well as crystal violet staining described previously (36).

Cross-reactivity of monoclonal antibodies generated against S. aureus CNA19—Murine monoclonal antibodies generated against CNA19 from S. aureus were screened by ELISA for their ability to recognize intact S. epidermidis. As shown in FIG. 9, mAb 11H11 recognized 5 different clinical isolates of S. epidermidis. Several other mAbs, including 3D3, 9A4, and 12H10, had lower but detectable binding.

Example 2

Characterization of Monoclonal Antibodies and Mapping of Epitopes

Initial characterization of monoclonal antibodies—22 monoclonal antibodies against CNA19 were isolated. The isotype of each of the 22 mAbs raised against CNA19 and 16H9, which was raised against the full-length A domain of CNA, CNA55, was determined (Table 2). The majority of the mAbs were of IgG$_1$-k type, six were of IgG$_{2a}$-k (2B3, 3D3, 7C2, 8H10, 11D5, and 11H11), and one (1F6) was of IgG$_{2b}$-k type.

ELISA assays were carried out to determine the apparent $K_D$ values for CNA19 of each of the 22 mAbs and 16H9 (Table 2). The majority of the mAbs showed similar $K_D$ value, at the $10^{-9}$ M range. 5G4 showed a slightly lower affinity with a $K_D$ of $2.9 \times 10^{-8}$ M and 8E6 a slightly higher affinity with a $K_D$ of $7.5 \times 10^{-10}$ M.

The percentage binding of $^{125}$I-collagen to immobilized CNA19 after the addition of 2 µg of each mAb was shown in FIG. 1. The 22 mAbs against CNA19 showed inhibitory effects on collagen binding of CNA19. Drastically reduced binding was observed upon the addition of these mAbs, while an anti-His-tag mAb, 7E8, did not inhibit binding. Except for 7E2, the mAbs inhibited collagen binding of CNA19 by at least 80%. 7E2 reduced binding by 57%. It seemed that there was not a direct correlation between the affinity of an mAb as determined by ELISA and its inhibition potency. Interestingly, mAb 16H9 showed the ability to enhance CNA19 binding to collagen (FIG. 1).

Mapping of epitopes recognized by blocking mAbs—To map the antigenic epitopes recognized by the 22 blocking mAbs, a set of overlapping synthetic peptides were made. Each of the peptides was 25-amino acids long and the whole set spanned the entire CNA19 sequence. However, none of the peptides reacted with any of the mAbs in ELISA assays (data not shown). This suggested that the mAbs recognized conformational epitopes. In order to make longer peptides that were more likely to adopt the conformations as in CNA19, a set of GST fusion constructs, each of which encoded a stretch of 50 to 55 amino acids of CNA19 sequence, were also constructed and the fusion peptides purified. None of the mAbs reacted with these fusion peptides (data not shown), suggesting that the GST-fusion peptides were still not able to fold into conformations that could be recognized by the mAbs.

Previous study by our group (14) showed that the amino acid sequence similarity between CNA and ACE, a collagen adhesin of E. faecalis, was primarily in the CNA19 region. The A domain (the binding domain) of ACE was predominantly composed of β-sheets as determined by its far-UV CD spectrum. When the corresponding region in ACE was analyzed using SwissModel, the predicted structure showed highly similar backbone conformation as that of CNA19 determined by X-ray crystallization. The corresponding region in ACE was then designated ACE19. FIG. 2A showed the result of ClustalW alignment of the amino acid sequences of CNA19 and ACE19 using the default parameters. The two sequences had 29% overall identity and 40% overall similarity. Higher homology was observed in regions correspond to CNA19 β-strands A, B, and H, and their flanking residues (7 out of 8, 8 out of 9 and 8 out of 13 residues, respectively, were similar). This is noteworthy since these strands form a major part of the collage-binding trench on one surface of CNA19 (20). The N-terminal portion of β-strands C and D were also highly similar, however, the remaining parts of these strands were less homologous. ACE19 was cloned and the purified ACE19 protein was tested for its reactivity with the 22 anti-CNA19 mAbs as well as 16H9 and 7E8 in ELISAs. It was found that except for 7E8, it did not react with any of the mAbs (Table 3). Thus, ACE19 was used as an "inert" template for constructing chimeric proteins with regions of CNA19 replaced by corresponding sequences from ACE19. These chimeras were then used to map the epitopes.

Initially, five chimeras containing approximately the N-terminal quarter (E), the N-terminal three-quarters (G), the central region (I), the C-terminal quarter (J) and the C-terminal three-quarters (L) of CNA19 sequence were generated (FIG. 2B). These chimeric proteins expressed well in the expression system and were soluble. Their far-UV CD spectra showed similar patterns to those of CNA19 and ACE19, suggesting similarities in the overall folding of these molecules (data not shown).

The chimeras were tested with the each of the 22 anti-CNA19 mAbs in ELISA assays. Except for chimera E, they showed good reactivity with some of the mAbs but not others (Table 3). All five chimeras, CNA19 and ACE19 reacted with 7E8, an anti-His-tag monoclonal antibody. We note that except for chimera E, the number of mAbs recognizing each chimera was approximately in proportion to the length of CNA19 sequence within each protein. This was taken as indicating that chimera G, I, J and L presented CNA19 epitopes in proper conformation.

Chimera G reacted with 17 mAbs (1F6, 2B1, 2B3, 3D3, 5G4, 7C2, 7E2, 7G2, 8E6, 8H10, 9A4, 9F11, 9G3, 9G7, 10G5, 11D5 and 11H11), but not with the remaining five (1H1, 3B12, 5D12, 5H1 and 12H10). Since in chimera G, the C-terminal quarter sequence of CNA19 was replaced by the relevant region of ACE19, the results suggested that the former 17 mAbs recognized epitopes at the N-terminal three-quarters of CNA19 from amino acid residue 151 to 284, whereas the latter five recognized epitopes at the C-terminal quarter from amino acid 285 to 318 (FIG. 2B). Chimera I reacted with 13 mAbs (1F6, 2B3, 3D3, 5G4, 7C2, 7E2, 7G2, 8E6, 8H10, 9A4, 9G7, 11D5 and 11H11), but not the others, suggesting that the 13 mAbs recognized epitopes at the central region of CNA19 while the remaining 9 were either at the N- or the C-terminal quarter. Similar reasoning was applied to chimera J and L. When the ELISA data of chimera G, I, J and L were combined, we were able to map the epitopes to different regions of CNA19. Eleven of the mAbs (2B3, 3D3, 5G4, 7C2, 7E2, 7G2, 8H10, 9A4, 9G7, 11D5, and 11H11) reacted with chimeras G, I, and L but not J, and therefore they were mapped to the central region of CNA19 from amino acid residue 187 to 284. 8E6, 9G3 and 10G5 reacted with chimeras G and L, but did not react with I or J, and they were mapped to the central region based on the region being common between the two chimeras. 8E6 and 9G3 were shown to react with chimera G, L and weakly with I in Western blot analysis (data not shown), consistent with the ELISA results. One of the mAbs, 1F6, reacted with chimeras G, I, and L, but also with J. Its reactivity with J, however, was weaker than that with G, I and L. Thus 1F6 was tentatively mapped to the central half. This was also confirmed by Western blot analysis using 1F6 with different chimeras (data not shown). In all, fifteen mAbs were found to recognize epitopes at the central region of CNA19 from residue 187 to 284 (the second residue of β-strand B to the last second residue of β-strand H).

Five mAbs (1H1, 3B12, 5D12, 5H1 and 12H10) reacted with chimeras J and L, but not with G or I, thus they were mapped to the C-terminal quarter of CNA19 from residue 283 to 318 (the last second residue of β-strand H to the 3' end). Based on reactions with chimera G, but not with 1, J or L, mAbs 2B1 and 9F11 were mapped to the N-terminal quarter of CNA19 from residue 151 to 193. However, they did not react with chimera E. This could be due to the high sequence similarity around β-strands A and B region between CNA19 and ACE19, resulting in a chimeric protein that was predominantly ACE19, and therefore the epitopes at the N-terminus in chimera E may not be presented in proper conformation.

To further map the epitopes, a second set of chimeras (N to X) was constructed. In chimeras N to V, the CNA19 sequence (from the N-terminal starting point of CNA19 sequence in chimera L towards the C-terminal end point of CNA19 sequence of chimera G) was gradually replaced by corresponding regions of ACE19. However, these chimeras showed varying degrees of poor solubility. When they were tested with the mAbs, only chimera N (FIG. 2B) showed reactions with relatively reasonable number of mAbs and its reactivity was lower than those observed for chimeras G, I, J and L (Table 3). Thus chimeras O to V were not further discussed. Chimera W and X were constructed to further map the epitopes mapped to the C-terminal quarter region of CNA19 (FIG. 2B) and they had good solubility. W showed reactivity with a large number of mAbs suggesting that it presented the epitopes properly (Table 3). Chimera X did not react with any of the mAbs, possibility due to a similar reason discussed for chimera E, that X contains very little CNA19 sequence.

The results from chimera W fully supported the conclusions obtained from the results of chimera G, I, J and L. All the 15 mAbs mapped to the central region and the two to the N-terminal quarter reacted with chimera W, while none of the five mAbs to the C-terminal quarter did, confirming the mapping results. Furthermore, the results suggested that the five mAbs previously mapped to the C-terminal quarter, recognized epitopes located within the last 21 amino acid residues at the very C-terminal end of CNA19.

The results from chimera N were largely consistent with previous conclusions. It reacted with 14 of the 15 mAbs mapped to the central region and did not with the two to the N-terminal quarter. The mAb in the central region that did not react with N was 10G5, which did not react well with some other chimeras either. One possibility was that 10G5 was extremely sensitive to changes in the conformation of the relevant epitope(s), so that slight variations led to loss of the reactivity. The other possibility was that the epitope(s) recognized by 10G5 was located at residue 187 to 207 (β-strand B to middle of β-strand C). The five mAbs mapped to the C-terminus of CNA19 did not react with chimera N, however, this was interpreted as due to improper folding of the relevant epitopes in chimera N, since the results from chimeras G, I, J, L and W clearly localized them to the C-terminus.

16H9, one of the mAbs that raised against CNA55, was found to react with CNA19, chimera G, I, L, N (weakly) and W. Thus, 16H9 was also mapped to the central half of CNA19 (Table 3).

In conclusion, the 22 inhibiting mAbs raised against CNA19 recognized conformationally-dependent epitopes and these epitopes were located throughout CNA19 (FIG. 3). This suggested that the entire molecule was involved in its interaction with collagen, either by directly contacting specific residues in collagen, or by adopting the proper conformation necessary for the accommodation of the collagen triple helix.

The 22 monoclonal antibodies inhibited collagen binding of S. aureus strain Cowan I—In order to see if the functionally relevant epitopes, mapped using the mAbs and the chimeras, were present in the full-length native protein displayed on S. aureus cell surface, we examined the ability of the mAbs to inhibit collagen binding of S. aureus strain Cowan I which expresses CNA, in liquid phase binding assays. All 22 mAbs inhibited Cowan I binding to soluble $^{125}$I-collagen, while 16H9 the anti-His-tag mAb, 7E8, did not (FIG. 4), indicating that the epitopes were present on the surface of Cowan I. A rough correlation between the ability to inhibit CNA19 and Cowan I binding to collagen was observed. For example, mAbs 9G7 and 11H11, two of the good inhibitors of CNA19, also inhibited Cowan I binding to collagen effectively (FIG. 5), binding was almost completely inhibited with 1 µg of the antibody. 8E6, a moderate inhibitor of CNA19, inhibited collagen binding of Cowan I less effectively, binding was reduced by only over 50% with 0.5 µg of 8E6, and greater inhibition was observed with the use of over 2.5 µg antibody (FIG. 5). 16H9 did not inhibit Cowan I binding to soluble collagen (FIG. 4).

To examine if the mAbs could inhibit the adherence of S. aureus, the inhibitory effect of several mAbs on Cowan I attachment to immobilized collagen was also examined (FIG. 6). Of the ones tested, all showed inhibitory activity although to various extent, and the results were consistent with those observed for soluble collagen. For example, 9G7 and 11H11 inhibited the attachment of Cowan I to collagen effectively, while 8E6 did poorly. 16H9 did not inhibit bacteria attachment as expected (FIG. 6).

Cross-reactivity of monoclonal antibodies generated against *S. aureus* CNA19—As shown above, the cross-reactivity of murine monoclonal antibodies raised against *S. aureus* CNA19 was established by virtue of ELISA screening which tested the their ability to recognize intact *S. epidermidis*. As shown in FIG. 9, mAb 11H11 recognized 5 different clinical isolates of *S. epidermidis*. Several other mAbs, including 3D3, 9A4, and 12H10, had lower but detectable binding. Accordingly, the cross-reactivity of antibodies raised against *S. aureus* so as to be useful against *S. epidermidis* has been shown, and thus the CNA19 antibodies discussed herein can be useful against a plurality of *Staphylococcus* bacteria.

Displacement of *S. aureus* Cowan I from collagen by the mAbs—To test the possibility if the inhibiting mAbs could displace *S. aureus* from preformed collagen-bacteria complex, *S. aureus* Cowan I was incubated with $^{125}$I-collagen for an hour to allow the formation of the complex. Various amounts of mAbs were then added to the washed complex, and the decrease of $^{125}$I in the cell pellet was taken as indicating the dissociation of the collagen-bacteria complex.

All the mAbs were able to release collagen from collagen-bacteria complex to various extents, while anti-His tag antibody 7E8 and 16H9 were not. The residual collagen binding after the addition of 1 µg and 5 µg of each mAb was shown in FIG. 7. mAbs 1F6, 1H1, 2B1, 3B12, 5D12, 5H1, 7E2, 7G2, 9A4, 9G3, and 9G7 were able to release at least 86% of bound collagen with 1 µg antibody, and at least 96% bound collagen with 5 µg antibody. 9F11 and 12H10 were able to release 54% and 72% bound collagen with 1 µg antibody and 95.3% and 95.5% collagen with 5 µg antibody, respectively. The other mAbs were not as potent displacers as the ones mentioned above, 5G4, 8E6, 8H10, 10G5, 11D5 and 11H11 were able to release 8%, 14%, 24%, 46%, 12%, and 36% collagen with 1 µg antibody, 50%, 50%, 79%, 71%, 48%, and 53% collagen with 5 µg antibody, respectively. There was not a consistent correlation between the ability of the mAbs to release collagen from collagen-bacteria complex and the effectiveness of the mAbs to inhibit collagen binding. Among the good inhibitors, some (such as 3B12 and 9G7) were also good displacers, while others (such as 8H10 and 11H11) were poor displacers. Poor inhibitors generally showed poor displacing activities. The displacing effects of 9G7, 11H11, 8E6 and 16H9 at various concentrations were shown in FIG. 8A.

To test whether the mAbs could detach *S. aureus* from the surface of immobilized collagen, several mAbs were examined. Cowan I was first allowed to adhere to immobilized collagen and then increasing amount of the mAbs were added. Bacteria that remain attached were detected by using rabbit-anti mouse antibodies. The results were consistent with those from the displacement of soluble collagen from bacteria-collagen complexes. For example, 9G7 again showed strong displacing capability while 11H11 and 8E6 remained to be moderate or poor displacers and 16H9 did not displace (FIG. 8B). The ability of mAb 9G7 to displace Cowan I from the surface of immobilized collagen was assayed again using a different type of secondary antibody (goat-anti rabbit), or crystal violet for the detection of bacteria. Similar results were obtained (data not shown).

Example 3

In Vitro Demonstration of Mab Efficacy

Antibody Scale-Up and Purification

Hybridoma cells were grown in RPMI/DMEM, 1× Nutridoma-SP media containing 2 mM sodium pyruvate, 4 mM L-glutamine and 2× penicillin-streptomycin to 2–3 liter culture volumes. Hybridoma supernatants were then harvested by centrifugation. The supernatants were filtered through 0.45 µM filters and the IgG was affinity purified using protein G chromatography. The monoclonal antibodies was eluted using 0.1M glycine, pH 2.7 and immediately neutralized with one tenth volume of 2M Tris, pH 8.0. The purified IgG was then dialyzed against 1×D-phosphate buffered saline, pH 7.4. If needed, the purified antibody was concentrated and aliquots frozen.

*S. aureus*

*S. aureus* strain Barnett was isolated from a patient with osteomyelitis. *S. aureus* bacterial cells from a frozen glycerol stock were streaked onto a single blood agar plate. Single colonies from the initial plate were then restreaked on approximately 30 blood agar plates and placed in the 37° C. incubator for 24 hrs. The bacteria were scraped off the plates and placed in a 50 ml tube containing 10 mls of sterile 1×PBS and gently vortexed to remove the bacteria from the scraper. After scraping all plates an additional 10 mls sterile 1×PBS was added and the bacterial suspension was vortexed vigorously to facilitate separation of any agar debris from the bacteria. The bacterial suspension was then centrifuged at 3500×g at 4° C. for 10 minutes in the RC3C centrifuge. The supernatant was decanted and the bacterial pellet was resuspended in 20 mls of sterile 1×PBS. The pellet was washed twice with PBS. Finally, the bacterial pellet was resuspended in 10 mls freezing media (1×D-PBS, pH 7.4; 10% DMSO; 5% BSA) and then add the additional volume of freezing media for desired volume and 1 ml aliquots were snap frozen in ethanol/dry ice bath and placed in a −80° C. freezer. On the day of injection, the frozen bacterial stock was thawed and diluted 1:20 in sterile PBS. An aliquot of the challenge inoculum was plated on blood agar plates to determine the actual CFUs.

Animal Sex, Species, Number, Age and Source

Female Balb/C mice (5–6 weeks of age) were purchased from Taconic Quality Laboratory Animals and Services for Research (Germantown, N.Y.). Animals were allowed to acclimate for at least 14 days prior to initiation of treatment. Upon arrival, the mice were examined, group housed (5/cage) in polycarbonate shoe box cages with absorbent bedding. All mice were placed on a 12 hour light-dark cycle under the required husbandry standards found in the NIH Guide for the Care and Use of Laboratory Animals.

Identification and Randomization

All animals were uniquely identified using tail tattoos prior to dosing. Prior to initiation of treatment, the animals were individually weighed and their health was evaluated. Mice were randomized and assigned to treatment groups using stratified body weights.

Experimental Design

On Day-1, animals were treated with a single 0.5 ml IP injection of monoclonal antibody 9G3, 3B12, or were untreated. On Day 0, ≈7×10$^7$ CFU *S. aureus* were administered by a single IV injection (0.1 ml) to all animals via the tail vein.

Twenty-four hours after IgG administration, the mice were challenged with a single intravenous (IV) injection of S. aureus (Strain Barnett). The mice were followed for 10 days at which point all remaining mice were sacrificed. Significant differences in the survival times between treatment groups were detected. In the first experiment sixty-seven percent (20/30) of the mice that received 9G3 (p=0.0002 vs. control; Mantel-Cox test for survival time) survived the bacterial challenge. Only 20% (4/18) of the untreated mice treated survived the entire study period (FIG. 10). In the second experiment seventy percent (14/20) of the mice that received 3B12 (p=0.03 vs. control; Mantel-Cox test for survival time) survived the bacterial challenge (FIG. 11). In contrast, only 27% of the control mice survived the ten day study. These results clearly indicate that MSCRAMM specific monoclonal antibodies provide a significant level of protection against lethal infection of S. aureus.

Example 4

Sequence Information

Isolation and Sequencing of Variable Region Sequences:

Sequences for both the variable light chain and the variable heavy chain of a monoclonal antibody for CNA19 were determined as follows:

Messenger RNA was isolated from CNA 3B12 hybridoma cells using the Fast Track 2.0 kit (Invitrogen; catalog # K4500). Briefly, $1.4 \times 10^8$ hybridoma cells cultured in DMEM-10 medium with 10% FBS were washed with PBS, pelleted by centrifugation then lysed in detergent containing Protein/RNase Degrader. PolyA$^+$ mRNA was isolated by affinity purification on oligo-dT cellulose. Synthesis of first strand cDNA was accomplished using 5 µg of mRNA and reverse transcriptase in a cDNA synthesis kit (Novagen; catalog #69001-3) containing 20 pmol of 3' oligonucleotide mouse-specific primers (Novagen; catalog #'s 69796 and 69812) for each variable heavy and variable light chain. A portion (5 to 50 ng) of the cDNA was amplified by the polymerase chain reaction (PCR) using the PCR Reagent System (Life Technologies; catalog #10198-018) and a mouse variable heavy and light chain specific primer set (Novagen; catalog #70081-3, 5 pmol each) for 30 cycles (94° C. hot start, then cycles of 94° C. for 1 min, 50° C. for 1 min and 72° C. for 1 min). PCR products were fractionated electrophoretically in a 1% ultra pure agarose gel in sodium acetate buffer and visualized by ethidium bromide staining. PCR fragments matching the predicted size were excised from the gel and purified using BIO 101 Geneclean spin columns (catalog #1101-400) for ligation into the pCR2.1-TOPO (Invitrogen) plasmid, followed by transformation into competent TOP10 E. coli. (Invitrogen; catalog #K4500). After isolating plasmid DNA using QIAprep Spin Miniprep Kit (QIAGEN; catalog #27106), positive clones with inserts were identified by restriction endonuclease digestion and agarose gel electrophoresis, followed by sequencing on an ABI automated sequencer using M13 Forward and M13 Reverse primers. The resulting sequences were as follows:

3B12VLG-4 (Variable Light Sequence)

GAAGTTGTGATGACCCAAACTC-
CACTCTCCCTGCCTGTCAGTCTTGGCGATCACGC
CTCCATCTCTTGCAGATCTAGTCAGCGC-
CTTGTACACAGTMTGAAAACACCTATTT ACATTGG-
TATCTGCAGMGCCAGGCCAGTCTC-
CAAAGCTCCTGATCTACAAAGTTT
CCMCCGATTTTCTGGGGTCCCAGACAG-
GTTCAGTGGCAGTGGATCAGGGACAGA TTTCA-
CACTCAAGATCAGCAGAGTGGAGGCT-
GAGGATCTGGGAGTTTATTTCTGCT
CTCAAAGTACGCATGTTCCTCCCACGT-
TCGGAGGGGGGACCAGGCTGGAAATAAA A (SEQ ID NO. 1).

EWMTQTPLSLPVSLGDHASISCRSSQR-
LVHSNENTYLHWYLQKPGQSPKLLIYKVSN RFS-
GVPDRFSGSGSGTDFTLKISRVE-
AEDLGVYFCSQSTHVPPTFGGGTRLEIK (SEQ ID NO. 2)

Amino acids representing a CDR are underlined

3B12VHB-1 (Variable Heavy Sequence)

CAGGTTCAGCTGCAGCAGTCTGGAGCT-
GAGCTGATGAAGCCTGGGGCCTCAGTG
AAGATCTCCTGCMGGCTGCTGGCTACA-
CATTCAGTCCCTACTGGATAGAGTGGTT AAAGCA-
GAGGCCTGGACATGGCCTTGAGTGGAT-
TGGAGAGATTTTACCTGGAAGT
GGAAATATTAACTACMTGAGMGTTCMG-
GACAAGGCCACATTCACTGCTGATAC ATCCTCCAA-
CACAGTTTACATGCAAGTCAGCAGCCT-
GACATCTGAGGACTCTGCCG
TCTATTACTGTGCAAGAGAGGAGGATG-
GTTACCCGGCCTGGTTTGCTTACTGGGG CCAAGG-
GACTCTGGTCACTGTCTCTGCA (SEQ ID NO. 3).

QVQLQQSGAELMKPGASVKISCK-
AAGYTFSPYWIEWLKQRPGHGLEWIGEILPGSGNI
NYNEKFKDKATFTADTSSNTVYMQVSS-
LTSEDSAVYYCAREEDGYPAWFAYWGQGT LVTVSA (SEQ ID NO. 4).

Amino acids representing a CDR are underlined

Example 5

Further Characterization of mAb's Generated Against CNA19

A. Blocking Activity of mAbs Generated Against CNA19 [CBD (151–318)] on Adherence of S. aureus to Immobilized Collagen.

As described above, all of the members of the mAbs raised against the CNA19 region, or residues 151–318 of the collagen binding domain (CBD), inhibited binding of $^{125}$I-collagen to cells of S. aureus Cowan I. When bacteria were assayed for the ability to attach to collagen in the presence of increasing concentrations of each mAb, it was found that the antibodies 3B12, 3D3, 8E6, 11H11, 12H10, 7C2, 9G7, and 5G4 blocked staphylococcal adherence. The inhibitory activity of mAbs 9G7, 7C2 and 3B12 appeared more effective as compared to the antibody 8E6, as indicated in FIGS. 12A and 12B.

B. Displacement of Collagen Complexed with S. aureus Cells by mAbs.

To examine the role of each mAb in displacing collagen from the bacteria-collagen complex, $^{125}$I-labeled collagen was initially allowed to bind S. aureus cells. Bacteria were harvested by centrifugation and then added and incubated with increasing concentrations of each antibody. Finally, the radioactivity bound to the cells was determined in a γ counter. In these experimental conditions a large portion of the $^{125}$-I collagen bound to the bacteria could be displaced from the cells by addition of each mAb. The monoclonal antibodies 1F6, 1H1, 2B1, 3B12, 9A4 and 9G7 showed to be very effective displacers, whereas the mAbs 5G4, 8E6, 11D5 and 11H11 weakly affected dissociation of the ligand from the bacterial cells (see FIGS. 12A, 12B, and 13).

The time course of the displacement reaction conducted with mAb 3B12 is shown in the inset of FIG. 13 inset. Bacteria were first incubated with $^{125}$I-labeled collagen. Subsequently, staphylococci were harvested by centrifugation, added to 1 μg of the mAb 3B12 and incubated for increasing periods of time. Following 5 min. incubation, a rapid displacement of the majority of the radiolabeled ligand was observed.

The dissociation of the bacteria-ligand complexes by the mAbs could also be demonstrated in an assay where staphylococci were allowed to adhere to immobilized collagen (FIGS. 14A–C). When increasing concentrations of the mAbs 3B12, 3D3, 7C2, and 9G7 were added to S. aureus cells adhering to immobilized collagen, bacteria were promptly displaced from the wells. The antibodies 12H10 and 11H11 promoted a moderate displacement, wherein mAbs 8E6 and 5G4 poorly dissociate the complex.

To gain further insights on the displacement reaction, the $K_D$ values for each mAb were determined as shown in Table 2. Mabs having a relatively low affinity for CBD (151–318) exhibited a strong displacement activity and vice versa. Thus, the efficiency with which each mAb displaces the ligand from the bacteria-collagen complex does not seem to correlate with the $K_D$ values. Conversely, these data support the concept that CNA19 (CBD 151–318) may have low and high affinity conformational states and that "displacer antibodies" could stabilize the low conformational state. However, it cannot be excluded that binding of "displacer antibody" to CNA19 induces a conformational change to the trench which results in a state incompatible with ligand binding.

Whatever the mechanism may be, this information highlights the clinical significance and the therapeutic value of the monoclonal antibodies to CNA19 in accordance with the present invention, particularly antibodies 3B12, 3D3, 7C2 and 9G7, which effectively inhibit and displace the ligand from bacteria. Thus it is contemplated in accordance with the present invention that these antibodies will be useful both in prophylactic methods as well as methods of treating patients affected by S. aureus and S. epidermidis infections.

Example 6

Additional Families of CBD Antibodies and Reactivity to the CNA19 Region

A. Properties of mAbs Against CBD (30–529).

A new family of mAbs against CBD (30–529) (or M55) was generated, and eight stable hybridomas were obtained that produced and secreted antibodies which reacted with the recombinant A domain of CNA. The class of antibodies is reported in Table 4. The relative reactivity of the different mAbs to the antigen was assessed in an enzyme-linked immunosorbent assay (ELISA) where the full length A domain of CNA was coated in microtiter wells and incubated with increasing concentrations of each mAb. The amount of the antibody bound to the adsorbed antigen reached a plateau and the apparent $K_D$ (dissociation constant) values for these interactions were estimated from the concentrations required for half-maximal signal (Table 5).

B. Localization of the Epitopes Recognized by the Different mAbs.

To localize the epitopes recognized by the generated mAbs, different segments of the A domain were tested for their ability to support antibody binding in ELISA and Western blot. As expected, the results of these experiments revealed that all the mAbs reacted with the native receptor (except the antibody 1C9) and CBD (50–329). Three mAbs, 2B8, 16H9 and 1C9, also reacted with CBD (61–343) and CBD (151–318) (CNA19). Moreover, 2B8 and, to a minor extent, 1C9, recognized the corresponding epitopes in CBD (151–297) (Table 6). To further locate the antigenic determinants for the mAbs which reacted with the CBD (151–318) CNA19 domain in the initial mapping, a series of GST-CNA derivatives spanning the CBD (151–318) segment of the collagen adhesin were constructed. None of the recombinant proteins obtained were recognized in ELISA by the mAbs 16H9 and 2H8 although they showed good reactivity toward a serum containing IgG raised against CBD (151–318), as shown in FIG. 15A. Together, these data suggest that these epitopes are conformational.

To map conformational epitopes in CBD (151–318) for the mAbs 2B8 and 16H9, five chimeras consisting of segments of ACE19 (174–319) and CNA19 (151–318) were constructed. As shown in FIG. 15B, the reactivity of chimeras G, I and L for the antibody 16H9 suggests the localization of the antibody-binding site in the central half of CBD (151–318). The exclusive recognition of chimera L by 2B8 indicates the epitope location in the central half of the fusion protein. Alternatively, the possibility cannot be ruled out that the antigenic determinant maps to the C-terminal end of CBD (151–318). In both cases, a role of the flanking regions in inducing epitope formation seems to be required.

C. Effect on mAbs on Ligand Binding.

The anti CBD (30–529) mAbs were examined for their effects on collagen binding to S. aureus cells. Binding inhibition assay was used in which bacteria and $^{125}$I-collagen were incubated in the presence of each mAb. Only mAbs 2B8 and 1A11 inhibited binding of the ligand to staphylococci at some extent (FIG. 15C). MAbs 2B8 and 1A11 inhibited collagen binding to S. aureus up to 60% and, when combined together at highest concentrations, blocked ligand binding almost completely. The two mAbs also shared the property to moderately displace collagen from bacterial-collagen complexes (FIG. 15D).

Example 7

Monoclonal Antibody 3B12 Recognition of Native CNA Expressed by S. aureus Clinical Isolates Method Summary:

Bacterial Preparation—10 ml tryptic soy broth overnight cultures were prepared from a single colony off a streak plate prepared from frozen stocks. The following morning 10 ml of tryptic soy broth was inoculated with 50 ul of overnight stock and grown for three hours. All cultures were stored on ice after growth period. All cultures were normalized to approximately the same OD.

Blocking of Protein A—All cultures were incubated for 30 minutes on ice in 10 ml of a 1:100 dilution (0.116 mg/ml) of rabbit IgG in 1×PBS. Bacteria were washed once in 10 cold 1×PBS by centrifugation at 3000 rpm for 10 minutes. They were resuspended in 2.5% BSA in 1×PBS (PBSA) and stored on ice.

Antibody Preparation—10 mls of 8 μg/ml mAb in PBSA were prepared for each antibody and supernatant. Solutions were stored on ice Primary Ab Incubation—The assay was performed in 144 titertubes for ease in handling. Using a multi-channel pipette, 20 µl of bacteria were added each tube. 0.5 ml of 8 µg/ml Ab solution was then added to the designated tubes. All tubes were vortexed and incubated on ice for 30 minutes. Following the incubation each tube was vortexed and then centrifuge in plate rotor at 3000 RPM for 10 minutes. The supernatant was decanted by hand for each tube. The bacteria were washed twice in cold PBSA.

Secondary PE F(ab')$_2$ Incubation—Each tube received 0.5 ml of a 1:200 dilution of secondary antibody. The bacteria were resuspended and mixed by vortexing. The tubes were incubated on ice for 30 minutes vortexing twice at ten minute intervals. Following this incubation the bacteria were washed twice with a final resuspension in PBSA. The tubes were stored on ice until FACS analysis.

FACS Analysis—Each titertube (144) was transferred to a 12×75 mm flow tube. The instrument was calibrated and the FL-2 detector was adjusted so that the isotype control PE emission was detected in the first decade of the FL-2 histogram scale.

Staining Profiles—The histogram representations of FIGS. 16A–D illustrate the staining profiles of each strain at 3 hr and overnight culture time points with each monoclonal.

Results—These tests provided examples of recognition of native collagen MSCRAMM on *S. aureus* strains by mAb 3B12 in accordance with the present invention.

| Primers | Sequence 5'- 3' # |
|---|---|
| CNA19 5' | GAA<u>GGATCC</u>ATAACATCTGGGAATAAATC |
| CNA19 3' | GTT<u>GTCGAC</u>*TCA*ATTGTGCACAGTATG |
| ACE19 5' | GAA<u>GGATCC</u>ACAGCAACGGCGACTC |
| ACE19 3' | GTT<u>GTCGAC</u>*TCA*ATTTTTAACCTGTGATG |
| ACE19E | CATGTACGATGGTTTTTAAATGTGAAC |
| M19E | ATTTAAAAACCATCGTACATGTGTCGTATC |
| M19G | TTGGCCTGCTTCTGTGATTTTGGTTTTGTAGTTAAT |
| ACE19G | ATTAACTACAAAACCAAAATCACAGAAGCAGGCCAA |
| M19I | TCAAATCAAGTACGTTGGTTTTTAAATATTAAC |
| ACE19I | GTTAATATTTAAAAACCAACGTACTTGATTTGA |
| M19J | GTCCGTTACACTTCGACAATTACGAATGAACAGCAA |
| ACE19J | TTGCTGTTCATTCGTAATTGTCGAAGTGTAACGGAC |
| M19N | GAAGATATTTCAATTAAGGATCAGATTCAAGGTG |
| ACE19N | TTGAATCTGATCCTTAATTGAAATATCTTCTGTG |
| M19W | GTTTAGTTGATAATTAGCTTGTGAATTATTAACAAAC |
| ACE19W | AATAATTCACAAGCTAATTATCAACTAAACAATCAAG |
| M19X | AATAGTTATGACATCTGGTATCAAGAGCATGGTAAG |
| ACE19X | ATGCTCTTGATACCAGATGTCATAACTATTTTC |

Boldface letters indicate sequences from CNA19, underlined letters and italicised letters indicate restriction sites and stop codons added for cloning purposes.

TABLE 1B

Combination of primers and templates used for the construction of chimeras.

| | First round PCR | | | | Second round PCR |
|---|---|---|---|---|---|
| | Segment 1 | | Segment 2 | | |
| Chimeras | Template | Primers | Template | Primers | Primers |
| E | ACE19 | ACE19 5' ACE19E | CNA19 | CNA19E CNA19 3' | ACE19 5' CNA19 3' |
| G | CNA19 | CNA19 5' CNA19G | ACE19 | ACE19G ACE19 3' | CNA19 5' ACE19 3' |
| I | ACE19 | ACE19 5' ACE19I | ChimeraG | CNA19I ACE19 3' | ACE19 5' ACE19 3' |
| J | ACE19 | ACE19 5' ACE19J | CNA19 | CNA19J CNA19 3' | ACE19 5' CNA19 3' |
| L | ACE19 | ACE19 5' ACE19I | CNA19 | CNA19I CNA19 3' | ACE19 5' CNA19 3' |
| N | ACE19 | ACE19 5' ACE19N | CNA19 | CNA19N CNA19 3' | ACE19 5' CNA19 3' |
| W | CNA19 | CNA19 5' CNA19W | ACE19 | ACE19W ACE19 3' | CNA19 5' ACE19 3' |
| X | ACE19 | ACE19 5' ACE19X | CNA19 | CNA19X CNA19 3' | ACE19 5' CNA19 3' |

TABLE 2

Summary of the isotypes and the apparent $K_D$ values of the mAbs.

| Antibody | Isotype | $K_D$ (M) |
|---|---|---|
| 1F6 | IgG$_{2b}$-k | $6.7 \times 10^{-9}$ |
| 1H1 | IgG$_1$-k | $1.67 \times 10^{-9}$ |
| 2B1 | IgG$_1$-k | $1 \times 10^{-9}$ |
| 2B3 | IgG$_{2a}$-k | $2.1 \times 10^{-9}$ |
| 3B12 | IgG$_1$-k | $4.5 \times 10^{-9}$ |
| 3D3 | IgG$_{2a}$-k | $1.2 \times 10^{-9}$ |
| 5D12 | IgG$_1$-k | $6.45 \times 10^{-9}$ |
| 5G4 | IgG$_1$-k | $2.9 \times 10^{-8}$ |
| 5H1 | IgG$_1$-k | $7.5 \times 10^{-9}$ |
| 7C2 | IgG$_{2a}$-k | $2.73 \times 10^{-9}$ |
| 7E2 | IgG$_1$-k | $1.8 \times 10^{-9}$ |
| 7G2 | IgG$_1$-k | $1.15 \times 10^{-9}$ |
| 8E6 | IgG$_1$-k | $7.5 \times 10^{-10}$ |
| 8H10 | IgG$_{2a}$-k | $1.3 \times 10^{-9}$ |
| 9A4 | IgG$_1$-k | $2 \times 10^{-9}$ |
| 9F11 | IgG$_1$-k | $1.28 \times 10^{-9}$ |
| 9G3 | IgG$_1$-k | $1.02 \times 10^{-9}$ |
| 9G7 | IgG$_1$-k | $1.03 \times 10^{-9}$ |
| 10G5 | IgG$_1$-k | $2.17 \times 10^{-9}$ |
| 11D5 | IgG$_{2a}$-k | $2.17 \times 10^{-9}$ |
| 11H11 | IgG$_{2a}$-k | $3 \times 10^{-9}$ |
| 12H10 | IgG$_1$-k | $1.46 \times 10^{-9}$ |
| 16H9 | IgG$_1$-k | $5 \times 10^{-9}$ |

TABLE 3

Reactivity of the mAbs against CNA19, ACE19 and the chimeras[1].

| mAb | CNA19 | ACE19 | E | G | I | J | L | N | W | X |
|---|---|---|---|---|---|---|---|---|---|---|
| 7E8[2] | + | + | + | + | + | + | + | + | + | + |
| 1F6 | + | − | − | + | + | + | + | + | + | − |
| 1H1 | + | − | − | − | − | + | + | − | − | − |
| 2B1 | + | − | − | + | − | − | − | − | + | − |
| 2B3 | + | − | − | + | + | − | + | + | + | − |
| 3B12 | + | − | − | − | − | + | + | − | − | − |
| 3D3 | + | − | − | + | + | − | + | + | + | − |
| 5D12 | + | − | − | − | − | + | + | − | − | − |
| 5G4 | + | − | − | + | + | − | + | (+) | + | − |
| 5H1 | + | − | − | − | − | + | + | − | − | − |
| 7C2 | + | − | − | + | + | − | + | + | + | − |
| 7E2 | + | − | − | + | + | − | + | + | + | − |
| 7G2 | + | − | − | + | + | − | + | + | + | − |
| 8E6 | + | − | − | + | (+) | − | + | + | + | − |
| 8H10 | + | − | − | + | + | − | + | + | + | − |

TABLE 3-continued

Reactivity of the mAbs against CNA19, ACE19 and the chimeras[1].

| mAb | CNA19 | ACE19 | E | G | I | J | L | N | W | X |
|---|---|---|---|---|---|---|---|---|---|---|
| 9A4 | + | − | − | + | + | − | + | + | + | − |
| 9F11 | + | − | − | + | − | − | − | − | + | − |
| 9G3 | + | − | − | + | − | − | + | (+) | + | − |
| 9G7 | + | − | − | + | + | − | + | + | + | − |
| 10G5 | + | − | − | + | (+) | − | (+) | − | + | − |
| 11D5 | + | − | − | + | + | − | + | + | + | − |
| 11H11 | + | − | − | + | + | − | + | + | + | − |
| 12H10 | + | − | − | − | − | + | + | − | − | − |
| 16H9 | + | − | − | + | + | − | + | (+) | + | − |
| Total number of reacting mAbs[3] | 24 | 1 | 1 | 19 | 16 | 7 | 22 | 16 | 19 | 1 |

[1]The reactivities were determined using ELISA assays.
[2]7E8 is an anti-His tag monoclonal antibody.
[3]The number includes positive reactions with 7E8.
[4]Parentheses indicate weak reactions in ELISA assays.

TABLE 4

Isotyping of mAbs generated against CBD (30–529).

| mAb | Class |
|---|---|
| 1A11 | $IgG_1$-k |
| 1C9 | $IgG_1$-k |
| 2B8 | $IgG_1$-k |
| 8G9 | $IgG_1$-k |
| 10E8 | $IgG_1$-λ |
| 13C9 | $IgG_1$-k |
| 16H9 | $IgG_1$-k |
| 17D11 | $IgG_1$-k |

TABLE 5

Relative reactivity of monoclonal antibodies raised against CBD (30–529).

| Antibody | $K_D$ |
|---|---|
| 1A11 | $2.1 \times 10^{-10}$ |
| 1C9 | $3.8 \times 10^{-8}$ |
| 2B8 | $4 \times 10^{-8}$ |
| 8G9 | $2.7 \times 10^{-7}$ |
| 16H9 | $5 \times 10^{-8}$ |
| 17D11 | $2.5 \times 10^{-9}$ |

The apparent $K_D$ (dissociation constant) values were estimated from the concentration required for half-maximal signal.

TABLE 6

Mapping of the epitopes for the monoclonal antibodies generated against CBD (30-529).

| mAb | Native recept r | | CBD (30-529) | | CBD (61-343) | | CBD (151-318) | | CBD (151-297) | |
|---|---|---|---|---|---|---|---|---|---|---|
| | ELISA | Western blot | ELISA | Western blot | ELISA | Western blot | ELISA | Western blot | ELISA | Western blot |
| 1A11 | + | + | + | + | − | − | − | − | − | − |
| 1C9 | − | − | + | + | + | + | (+) | (+) | (+) | (+) |
| 2B8 | + | + | + | + | + | + | + | + | + | + |
| 8G9 | + | + | + | + | − | − | − | − | − | − |
| 10E8 | − | − | + | + | − | − | − | − | − | − |
| 13C9 | − | − | + | + | − | − | − | − | − | − |
| 16H9 | + | + | + | + | + | + | + | + | − | (+) |
| 17D11 | + | + | + | + | − | (+) | − | (+) | − | (+) |

REFERENCES

1. Voytek, A., Gristina, A. G., Barth, E., Myrvik, Q., Switalski, L., Hook, M., and Speziale, P. (1988) *Biomaterials* 9, 107–110
2. Switalski, L., Patti, J. M., Butcher, W., Gristina, A. G., Speziale, P., and Hook, M. (1993) *Mol. Microbiol.* 7(1), 99–107
3. Patti, J. M., Bremell, T., Krajewska-Pietrasik, D., Abdelnour, A., Tarkowski, A., Ryden, C., and Hook, M. (1994) *Infect. Immun.* 62(1), 152–161
4. Nilsson, I.-M., Patti, J. M., Bremell, T., Hook, M., and Tarkowski, A. (1998) *J. Clin. Invest* 101(12), 2640–2649
5. Carnoy, C., and Moseley, S. L. (1997) *Mol. Microbiol.* 23(2), 365–379
6. Schulze-Koops, H., Burkhardt, H., Heesemann, J., Mark, K. v. d., and Emmrich, F. (1992) *Infect. Immun.* 60(6), 2153–2159
7. Tamm, A., Tarkkanen, A.-M., Korhonen, T. K., Kuusela, P., Toivanen, P., and Skurnik, M. (1993) *Mol. Microbiol.* 10(5), 995–1011
8. Schulze-Koops, H., Burkhardt, H., Heesemann, J., Mark, K. v. d., and Emmrich, F. (1995) *Arthritis &Rheumatism* 38(9), 1283–1289
9. Sebghati, T. A. S., Korhonen, T. K., Hornick, D. B., and Clegg, S. (1998) *Infect. Immun.* 66(6), 2887–2894
10. Switalski, L. M., Butcher, W. G., Caufield, P. C., and Lantz, M. S. (1993) *Infect. Immun.* 61(10), 4119–4125
11. Love, R. M., McMillan, M. D., and Jenkinson, H. F. (1997) *Infect. Immun.* 65(12), 5157–5164
12. Podbielski, A., Woischnik, M., Leonard, B. A. B., and Schmidt, K.-H. (1999) *Mol. Microbiol* 31(4), 1051–1064
13. Holmes, A. R., Gilbert, C., Wells, J. M., and Jenkinson, H. F. (1998) *Infect Immun.* 66(10), 4633–4639
14. Rich, R. L., Kreikemeyer, B., Owens, R. T., LaBrenz, S., Narayana, S. V. L., Weinstock, G. M., Murray, B. E., and Hook, M. (1999) *J. Biol. Chem.* in press
15. Roos, S., Aleljung, P., Robert, N., Lee, B., Wadstrom, T., Lindberg, M., and Jonsson, H. (1996) *FEMS Microbiol. Lett.* 144, 33–38
16. Gripenberg-Lerche, C., Skurnik, M., Zhang, L., Soderstrom, K.-O., and Toivanen, P. (1994) *Infect. Immun.* 62(12), 5568–5575
17. Roggenkamp, A., Neuberger, H.-R., Flugel, A., Schmoll, T., and Heesemann, J. (1995) *Mol. Microbiol.* 16(6), 1207–1219

18. Speziale, P., Raucci, G., Visai, L., Switalski, L. M., Timpl, R., and Hook, M. (1986) *J. Bacteriol.* 167(1), 77–81
19. Patti, J. M., Boles, J. O., and Hook, M. (1993) *Biochemistry* 32(42), 11428–11435
20. Symersky, J., Patti, J. M., Carson, M., House-Pompeo, K., Teale, M., Moore, D., Jin, L., Schneider, A., DeLucas, L. J., Hook, M., and Narayana, S. V. L. (1997) *Nature structural biology* 4(10), 833–838
21. Patti, J. M., House-Pompeo, K., Boles, J. O., Garza, N., Gurusiddappa, S., and Hook, M. (1995) *J. Biol. Chem.* 270(20), 12005–12011
22. Emsley, J., King, S. L., Bergelson, J. M., and Liddington, R. C. (1997) *J. Biol. Chem.* 272(45), 28512–28517
23. Nolte, M., Pepinsky, R. B., Venyaminov, S. Y., Koteliansky, V., Gotwals, P. J., and Karpusas, M. (1999) *FEBS Lett.* 452, 379–385
24. Rich, R. L., Deivanayagam, C. C. S., Owens, R. T., C C Carson, M., Hook, A., Moore, D., J. Symerski, Yang, V. W.-C., Narayana, S. V. L., and Hook, M. (1999) submitted
25. Kamata, T., Liddington, R. C., and Takada, Y. (1999) *J. Biol. Chem.* 274(45), 32108–32111
26. Dickeson, S. K., Mathis, N. L., Rahman, M., Bergelson, J. M., and Santoro, S. (1999) *J. Biol. Chem.* 274(45), 32182–32191
27. Kapyla, J., Ivaska, J., Riikonen, R., Nykvist, P., Pentikainen, O., Johnson, M., and Heino, J. (2000) *J. Biol. Chem.* 275(5), 3348–3354
28. Smith, C., Estavillo, D., Emsley, J., Bankston, L. A., Liddington, R. C., and Cruz, M. A. (2000) *J. Biol. Chem.* 275(6), 4205–4209
29. Kolher, G., and Milstein, C. (1975) *Nature* 256(5517), 495–497
30. Sambrook, J., Fritsch, E. F., and Maniatis, T. (1989) *Molecular cloning, a laboratory manual*, 2nd Ed., Cold Spring Harbor Laboratory Press, Cold Spring Harbor, N.Y.
31. Chung, C. T., Niemela, S. Z., and Miller, R. H. (1989) *Proc. Natl. Acad. Sci. USA* 86, 2172–2175
32. Pace, C. N., Vajdos, F., Fee, L., Grimsley, G., and Gray, T. (1995) *Protein Science* 4, 2411–2423
33. Rich, R. L., Demeler, B., Ashby, K., Deivanayagam, C. C. S., Petrich, J. W., Patti, J. M., Narayana, S. V. L., and Hook, M. (1998) *Biochemistry* 37(44), 15423–15433
34. Strawitch, E., and Nimni, M. E. (1971) *Biochemistry* 10(21), 3905–3911
35. Switalski, L. M., Speziale, P., and Hook, M. (1989) *J. Biol. Chem.* 264(35), 21080–21086
36. Ni Eidhin, D., Perkins, S., Francois, P., Vaudaux, P., Hook, M., and Foster, T. J. (1998) *Mol. Microbiol.* 30(2), 245–257
37. Li, R., Rieu, P., Griffith, D. L., Scott, D., and Arnaout, M. A. (1998) *J. Cell Biol.* 143(6), 1523–1534
38. Oxvig, C., Lu, C., and Springer, T. A. (1999) *Proc. Natl. Acad. Sci. USA* 96, 2215–2220

---

What is claimed is:

1. An isolated cross-reactive monoclonal antibody which binds to an epitope that is recognized by monoclonal antibody 11H11 set forth as SEQ.ID.NO: 2 and SEQ.ID.NO: 4, wherein said antibody is cross-reactive to both *S. aureus* and *S. epidermidis*, and wherein said antibody is capable of inhibiting adhesion of *S. aureus* to collagen and displacing *S. aureus* bound to collagen.

2. An antibody according to claim 1, wherein said antibody inhibits collagen binding of a Staphylococcal bacteria selected from the group consisting of *S. aureus* and *S. epidermidis*.

3. An isolated monoclonal antibody which binds to an epitope that is recognized by monoclonal antibody 11H11 set forth as SEQ.ID.NO: 2 and SEQ.ID.NO: 4.

4. A diagnostic kit comprising an antibody according to claim 1 and a detectable label for detecting antibody binding.

5. A composition comprising an effective amount of the antibody of claim 1 and a pharmaceutically acceptable vehicle, carrier or excipient.

6. An isolated monoclonal antibody which binds to an epitope that is recognized by monoclonal antibody 11H 11 set forth as SEQ.ID.NO:2 and SEQ.ID.NO: 4, that is cross-reactive to both *S. aureus* and *S. epidermidis* which is generated against amino acids 151–318 of the collagen binding domain of the *S. aureus* CNA protein, and which is capable of inhibiting adhesion of *S. aureus* to collagen and displacing *S. aureus* bound to collagen.

7. A diagnostic kit for immunodetection comprising, in a suitable container, an antibody according to claim 6 and an immunodetection reagent.

8. A diagnostic kit according to claim 7 wherein said immunodetection reagent is a detectable label that is linked to said antibody.

* * * * *

SEQUENCE LISTING

<160> NUMBER OF SEQ ID NOS: 30

<210> SEQ ID NO 1
<211> LENGTH: 336
<212> TYPE: DNA
<213> ORGANISM: Staphylococcus aureus

<400> SEQUENCE: 1

```
gaagttgtga tgacccaaac tccactctcc ctgcctgtca gtcttggcga tcacgcctcc      60
atctcttgca gatctagtca gcgccttgta cacagtaatg aaaacaccta tttacattgg     120
tatctgcaga agccaggcca gtctccaaag ctcctgatct acaaagtttc caaccgattt     180
tctggggtcc cagacaggtt cagtggcagt ggatcaggga cagatttcac actcaagatc     240
agcagagtgg aggctgagga tctgggagtt tatttctgct ctcaaagtac gcatgttcct     300
cccacgttcg gagggggac caggctggaa ataaaa                                336
```

<210> SEQ ID NO 2
<211> LENGTH: 112
<212> TYPE: PRT
<213> ORGANISM: Staphylococcus aureus

<400> SEQUENCE: 2

```
Glu Val Val Met Thr Gln Thr Pro Leu Ser Leu Pro Val Ser Leu Gly
 1               5                  10                  15

Asp His Ala Ser Ile Ser Cys Arg Ser Ser Gln Arg Leu Val His Ser
                20                  25                  30

Asn Glu Asn Thr Tyr Leu His Trp Tyr Leu Gln Lys Pro Gly Gln Ser
            35                  40                  45

Pro Lys Leu Leu Ile Tyr Lys Val Ser Asn Arg Phe Ser Gly Val Pro
        50                  55                  60
```

-continued

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Pro Thr Phe Gly Gly Gly Thr Arg Leu Glu Ile Lys
            100                 105                 110

<210> SEQ ID NO 3
<211> LENGTH: 360
<212> TYPE: DNA
<213> ORGANISM: Staphylococcus aureus

<400> SEQUENCE: 3
caggttcagc tgcagcagtc tggagctgag ctgatgaagc ctggggcctc agtgaagatc      60
tcctgcaagg ctgctggcta cacattcagt ccctactgga tagagtggtt aaagcagagg     120
cctggacatg gccttgagtg gattggagag attttacctg gaagtggaaa tattaactac     180
aatgagaagt tcaaggacaa ggccacattc actgctgata catcctccaa cacagtttac     240
atgcaagtca gcagcctgac atctgaggac tctgccgtct attactgtgc aagagaggag     300
gatggttacc cggcctggtt tgcttactgg ggccaaggga ctctggtcac tgtctctgca     360

<210> SEQ ID NO 4
<211> LENGTH: 120
<212> TYPE: PRT
<213> ORGANISM: Staphylococcus aureus

<400> SEQUENCE: 4

Gln Val Gln Leu Gln Gln Ser Gly Ala Glu Leu Met Lys Pro Gly Ala
1               5                   10                  15

Ser Val Lys Ile Ser Cys Lys Ala Ala Gly Tyr Thr Phe Ser Pro Tyr
                20                  25                  30

Trp Ile Glu Trp Leu Lys Gln Arg Pro Gly His Gly Leu Glu Trp Ile
            35                  40                  45

Gly Glu Ile Leu Pro Gly Ser Gly Asn Ile Asn Tyr Asn Glu Lys Phe
        50                  55                  60

Lys Asp Lys Ala Thr Phe Thr Ala Asp Thr Ser Ser Asn Thr Val Tyr
65                  70                  75                  80

Met Gln Val Ser Ser Leu Thr Ser Glu Asp Ser Ala Val Tyr Tyr Cys
                85                  90                  95

Ala Arg Glu Glu Asp Gly Tyr Pro Ala Trp Phe Ala Tyr Trp Gly Gln
            100                 105                 110

Gly Thr Leu Val Thr Val Ser Ala
        115                 120

<210> SEQ ID NO 5
<211> LENGTH: 21
<212> TYPE: PRT
<213> ORGANISM: Staphylococcus aureus

<400> SEQUENCE: 5

Ile Thr Ser Gly Asn Lys Ser Thr Asn Val Thr Val His Lys Ser Glu
1               5                   10                  15

Ala Gly Thr Ser Ser
            20

<210> SEQ ID NO 6
<211> LENGTH: 115

```
<212> TYPE: PRT
<213> ORGANISM: Staphylococcus aureus

<400> SEQUENCE: 6

Val Phe Tyr Tyr Lys Thr Gly Asp Met Leu Pro Glu Asp Thr Thr His
1               5                   10                  15

Val Arg Trp Phe Leu Asn Ile Asn Asn Glu Lys Ser Tyr Val Ser Lys
                20                  25                  30

Asp Ile Thr Ile Lys Asp Gln Ile Gln Gly Gln Gln Leu Asp Leu
            35                  40                  45

Ser Thr Leu Asn Ile Asn Val Thr Gly Thr His Ser Asn Tyr Tyr Ser
        50                  55                  60

Gly Gln Ser Ala Ile Thr Asp Phe Glu Lys Ala Phe Pro Gly Ser Lys
65                  70                  75                  80

Ile Thr Val Asp Asn Thr Lys Asn Thr Ile Asp Val Thr Ile Pro Gln
                85                  90                  95

Gly Tyr Gly Ser Tyr Asn Ser Phe Ser Ile Asn Tyr Lys Thr Lys Thr
                100                 105                 110

Thr Asn Glu
        115

<210> SEQ ID NO 7
<211> LENGTH: 32
<212> TYPE: PRT
<213> ORGANISM: Staphylococcus aureus

<400> SEQUENCE: 7

Gln Gln Lys Glu Phe Val Asn Asn Ser Gln Ala Trp Tyr Gln Glu His
1               5                   10                  15

Gly Lys Glu Glu Val Asn Gly Lys Ser Phe Asn His Thr Val His Asn
                20                  25                  30

<210> SEQ ID NO 8
<211> LENGTH: 37
<212> TYPE: PRT
<213> ORGANISM: Enterococcus faecalis

<400> SEQUENCE: 8

Thr Ala Thr Ala Thr Gln Arg Leu Thr Ile Glu Gly Val Thr Asn Thr
1               5                   10                  15

Glu Thr Gly Gln Ile Glu Arg Asp Tyr Pro Phe Phe Tyr Lys Val Gly
                20                  25                  30

Asp Leu Ala Gly Glu
        35

<210> SEQ ID NO 9
<211> LENGTH: 52
<212> TYPE: PRT
<213> ORGANISM: Enterococcus faecalis

<400> SEQUENCE: 9

Ser Asn Gln Val Arg Trp Phe Leu Asn Val Asn Leu Asn Lys Ser Asp
1               5                   10                  15

Val Thr Glu Asp Ile Ser Ile Ala Asp Arg Gln Gly Ser Gly Gln Gln
                20                  25                  30

Leu Asn Lys Glu Ser Phe Thr Phe Asp Ile Val Asn Asp Lys Glu Thr
            35                  40                  45

Lys Tyr Ile Ser
        50
```

<210> SEQ ID NO 10
<211> LENGTH: 10
<212> TYPE: PRT
<213> ORGANISM: Enterococcus faecalis

<400> SEQUENCE: 10

Leu Ala Glu Phe Glu Gln Gln Gly Tyr Gly
1               5                   10

<210> SEQ ID NO 11
<211> LENGTH: 5
<212> TYPE: PRT
<213> ORGANISM: Enterococcus faecalis

<400> SEQUENCE: 11

Lys Ile Asp Phe Val
1               5

<210> SEQ ID NO 12
<211> LENGTH: 64
<212> TYPE: PRT
<213> ORGANISM: Enterococcus faecalis

<400> SEQUENCE: 12

Thr Asp Asn Asp Phe Asn Leu Arg Phe Tyr Arg Asp Lys Ala Arg Phe
1               5                   10                  15

Thr Ser Phe Ile Val Arg Tyr Thr Ser Thr Ile Thr Glu Ala Gly Gln
            20                  25                  30

His Gln Ala Thr Phe Glu Asn Ser Tyr Asp Ile Asn Tyr Gln Leu Asn
        35                  40                  45

Asn Gln Asp Ala Thr Asn Glu Lys Asn Thr Ser Gln Val Lys Asn Val
    50                  55                  60

<210> SEQ ID NO 13
<211> LENGTH: 28
<212> TYPE: DNA
<213> ORGANISM: Staphylococcus aureus

<400> SEQUENCE: 13
gaagatccat aacatctggg aataaatc                                              28

<210> SEQ ID NO 14
<211> LENGTH: 27
<212> TYPE: DNA
<213> ORGANISM: Staphylococcus aureus

<400> SEQUENCE: 14
gttgtcgact caattgtgca cagtatg                                               27

<210> SEQ ID NO 15
<211> LENGTH: 25
<212> TYPE: DNA
<213> ORGANISM: Enterococcus faecalis

<400> SEQUENCE: 15
gaaggatcca cagcaacggc gactc                                                 25

<210> SEQ ID NO 16
<211> LENGTH: 29
<212> TYPE: DNA
<213> ORGANISM: Enterococcus faecalis -continued

```
<400> SEQUENCE: 16
gttgtcgact caattttta  a cctgtgatg                                    29

<210> SEQ ID NO 17
<211> LENGTH: 27
<212> TYPE: DNA
<213> ORGANISM: Enterococcus faecalis

<400> SEQUENCE: 17
catgtacgat ggttttaaa tgtgaac                                         27

<210> SEQ ID NO 18
<211> LENGTH: 30
<212> TYPE: DNA
<213> ORGANISM: Staphylococcus aureus

<400> SEQUENCE: 18
atttaaaaac catcgtacat gtgtcgtatc                                     30

<210> SEQ ID NO 19
<211> LENGTH: 36
<212> TYPE: DNA
<213> ORGANISM: Staphylococcus aureus

<400> SEQUENCE: 19
ttggcctgct tctgtgattt tggttttgta gttaat                              36

<210> SEQ ID NO 20
<211> LENGTH: 36
<212> TYPE: DNA
<213> ORGANISM: Enterococcus faecalis

<400> SEQUENCE: 20
attaactaca aaaccaaaat cacagaagca ggccaa                              36

<210> SEQ ID NO 21
<211> LENGTH: 33
<212> TYPE: DNA
<213> ORGANISM: Staphylococcus aureus

<400> SEQUENCE: 21
tcaaatcaag tacgttggtt tttaaatatt aac                                 33

<210> SEQ ID NO 22
<211> LENGTH: 33
<212> TYPE: DNA
<213> ORGANISM: Enterococcus faecalis

<400> SEQUENCE: 22
gttaatattt aaaaccaac gtacttgatt tga                                  33

<210> SEQ ID NO 23
<211> LENGTH: 36
<212> TYPE: DNA
<213> ORGANISM: Staphylococcus aureus

<400> SEQUENCE: 23
gtccgttaca cttcgacaat tacgaatgaa cagcaa                              36

<210> SEQ ID NO 24
<211> LENGTH: 36
<212> TYPE: DNA
<213> ORGANISM: Enterococcus faecalis
```

```
<400> SEQUENCE: 24
ttgctgttca ttcgtaattg tcgaagtgta acggac                                36

<210> SEQ ID NO 25
<211> LENGTH: 34
<212> TYPE: DNA
<213> ORGANISM: Staphylococcus aureus

<400> SEQUENCE: 25
gaagatattt caattaagga tcagattcaa ggtg                                  34

<210> SEQ ID NO 26
<211> LENGTH: 34
<212> TYPE: DNA
<213> ORGANISM: Enterococcus faecalis

<400> SEQUENCE: 26
ttgaatctga tccttaattg aaatatcttc tgtg                                  34

<210> SEQ ID NO 27
<211> LENGTH: 37
<212> TYPE: DNA
<213> ORGANISM: Staphylococcus aureus

<400> SEQUENCE: 27
gtttagttga taattagctt gtgaattatt aacaaac                               37

<210> SEQ ID NO 28
<211> LENGTH: 37
<212> TYPE: DNA
<213> ORGANISM: Enterococcus faecalis

<400> SEQUENCE: 28
aataattcac aagctaatta tcaactaaac aatcaag                               37

<210> SEQ ID NO 29
<211> LENGTH: 36
<212> TYPE: DNA
<213> ORGANISM: Staphylococcus aureus

<400> SEQUENCE: 29
aatagttatg acatctggta tcaagagcat ggtaag                                36

<210> SEQ ID NO 30
<211> LENGTH: 33
<212> TYPE: DNA
<213> ORGANISM: Enterococcus faecalis

<400> SEQUENCE: 30
atgctcttga taccagatgt cataactatt ttc                                   33
```